United States Patent
Vaezy et al.

(10) Patent No.: US 8,414,494 B2
(45) Date of Patent: Apr. 9, 2013

(54) THIN-PROFILE THERAPEUTIC ULTRASOUND APPLICATORS

(75) Inventors: Shahram Vaezy, Seattle, WA (US); Jinfei Yu, Beijing (CN); Vesna Zderic, Washington, DC (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/065,768

(22) PCT Filed: Sep. 15, 2006

(86) PCT No.: PCT/US2006/036106
§ 371 (c)(1), (2), (4) Date: Dec. 8, 2008

(87) PCT Pub. No.: WO2007/035529
PCT Pub. Date: Mar. 29, 2007

(65) Prior Publication Data
US 2009/0112098 A1    Apr. 30, 2009

Related U.S. Application Data

(60) Provisional application No. 60/718,085, filed on Sep. 16, 2005, provisional application No. 60/825,610, filed on Sep. 14, 2006.

(51) Int. Cl.
*A61B 8/14* (2006.01)

(52) U.S. Cl.
USPC ............................ 600/459; 600/427; 600/439

(58) Field of Classification Search .................. 600/446, 600/439, 427, 471, 459
See application file for complete search history.

(56) References Cited

U.S. PATENT DOCUMENTS

| 385,256 A | 6/1888 | Eggers |
| 2,992,553 A | 7/1961 | Joy ................................ 73/644 |

(Continued)

FOREIGN PATENT DOCUMENTS

| DE | 04230415 | 3/1994 |
| EP | 0 420 758 | 4/1991 |

(Continued)

OTHER PUBLICATIONS

Beard, Ralph E., Richard L. Magin, Leon A. Frizzell, and Charles A. Cain. "An Annular Focus Ultrasonic Lens for Local Hyperthermia Treatment of Small Tumors" *Ultrasound in Med. & Biol.* vol. 8, No. 2, pp. 177-184, 1982.

(Continued)

*Primary Examiner* — Tse Chen
*Assistant Examiner* — Joel F Brutus
(74) *Attorney, Agent, or Firm* — Kilpatrick Townsend & Stockton LLP

(57) ABSTRACT

An ultrasound therapy probe including a thin-profile therapy head for implementing therapeutic procedures in confined spaces. The thin-profile is achieved by incorporating a cooling fluid channel about a periphery of at least a portion of the housing. A therapy transducer is disposed in an inner volume of the housing, and fluid circulated through the peripheral cooling channel can be used to remove heat generated by the therapy transducer, without requiring bulky external cooling devices, such as balloons. The housing can include an acoustic lens portion, to enable the housing to be used with flat transducers and can also be configured to be used with concave transducers, and so that an acoustic lens is not required. Electrical connections can be made with conductors that extend through an elongate hollow handle.

29 Claims, 10 Drawing Sheets

U.S. PATENT DOCUMENTS

| | | | | |
|---|---|---|---|---|
| 4,059,098 A | 11/1977 | Murdock | | 128/2 |
| 4,484,569 A | 11/1984 | Driller et al. | | 128/60 |
| 4,545,386 A | 10/1985 | Hetz et al. | | 600/462 |
| 4,601,296 A | 7/1986 | Yerushalmi | | 607/156 |
| 4,688,578 A | 8/1987 | Takano et al. | | 128/660 |
| 4,708,836 A | 11/1987 | Gain et al. | | 264/40.1 |
| 4,773,865 A | 9/1988 | Baldwin | | 434/268 |
| RE33,590 E | 5/1991 | Dory | | 128/999.999 |
| 5,039,774 A | 8/1991 | Shikinami et al. | | 528/60 |
| 5,065,742 A | 11/1991 | Belikan et al. | | 128/24 |
| 5,080,101 A | 1/1992 | Dory | | 128/999.999 |
| 5,080,102 A | 1/1992 | Dory | | 128/999.999 |
| 5,088,498 A | 2/1992 | Beach et al. | | 600/453 |
| 5,150,712 A | 9/1992 | Dory | | 128/999.999 |
| 5,170,790 A | 12/1992 | Lacoste et al. | | 600/437 |
| 5,178,148 A | 1/1993 | Lacoste et al. | | 600/439 |
| 5,183,046 A | 2/1993 | Beach et al. | | 600/453 |
| 5,194,291 A | 3/1993 | D'Aoust et al. | | 148/276 |
| 5,215,680 A | 6/1993 | D'Arrigo | | 516/11 |
| 5,219,401 A | 6/1993 | Cathignol et al. | | 128/999.999 |
| 5,230,334 A | 7/1993 | Klopotek | | 128/999.999 |
| 5,289,820 A | 3/1994 | Beach et al. | | 600/443 |
| 5,311,869 A | 5/1994 | Okazaki | | 128/999.999 |
| 5,391,140 A | 2/1995 | Schaetzle et al. | | 601/4 |
| 5,394,877 A | 3/1995 | Orr et al. | | 600/459 |
| 5,471,988 A | 12/1995 | Fujio et al. | | 128/660.03 |
| 5,474,071 A | 12/1995 | Chapelon et al. | | 600/439 |
| 5,492,126 A | 2/1996 | Hennige et al. | | 600/439 |
| 5,507,790 A | 4/1996 | Weiss | | 607/100 |
| 5,520,188 A | 5/1996 | Hennige et al. | | 128/999.999 |
| 5,522,878 A | 6/1996 | Montecalvo et al. | | 607/152 |
| 5,526,815 A | 6/1996 | Granz et al. | | 128/999.999 |
| 5,534,232 A | 7/1996 | Denes et al. | | 422/186.26 |
| 5,536,489 A | 7/1996 | Lohrmann et al. | | 424/9.52 |
| 5,558,092 A | 9/1996 | Unger et al. | | 128/999.999 |
| 5,573,497 A | 11/1996 | Chapelon | | 601/2 |
| 5,609,485 A | 3/1997 | Bergman et al. | | 434/262 |
| 5,638,823 A | 6/1997 | Akay et al. | | 600/528 |
| 5,657,760 A | 8/1997 | Ying et al. | | 128/999.999 |
| 5,666,954 A | 9/1997 | Chapelon et al. | | 600/439 |
| 5,716,374 A | 2/1998 | Francese et al. | | 606/207 |
| 5,720,286 A | 2/1998 | Chapelon et al. | | 600/439 |
| 5,720,287 A * | 2/1998 | Chapelon et al. | | 600/439 |
| 5,726,066 A | 3/1998 | Choi | | 438/3 |
| 5,755,228 A | 5/1998 | Wilson et al. | | 128/660.06 |
| 5,762,066 A | 6/1998 | Law et al. | | 600/439 |
| 5,769,790 A | 6/1998 | Watkins et al. | | 600/439 |
| 5,807,285 A | 9/1998 | Vaitekunas | | 601/2 |
| 5,810,007 A | 9/1998 | Holupka et al. | | 600/439 |
| 5,817,021 A | 10/1998 | Reichenberger | | 600/439 |
| 5,823,962 A | 10/1998 | Schaetzle et al. | | 600/439 |
| 5,824,277 A | 10/1998 | Campos | | 423/242.1 |
| 5,827,204 A | 10/1998 | Grandia et al. | | 601/2 |
| 5,833,647 A | 11/1998 | Edwards | | 604/22 |
| 5,840,028 A | 11/1998 | Chubachi et al. | | 600/437 |
| 5,846,517 A | 12/1998 | Unger | | 424/9.52 |
| 5,853,752 A | 12/1998 | Unger et al. | | 424/450 |
| 5,873,828 A | 2/1999 | Fujio et al. | | 600/439 |
| 5,879,314 A | 3/1999 | Peterson et al. | | 601/2 |
| 5,882,302 A | 3/1999 | Driscoll, Jr. et al. | | 600/371 |
| 5,895,356 A | 4/1999 | Andrus et al. | | 600/439 |
| 5,897,495 A | 4/1999 | Aida et al. | | 600/411 |
| 5,906,580 A | 5/1999 | Kline-Schoder et al. | | 600/459 |
| 5,919,139 A | 7/1999 | Lin | | 600/443 |
| 5,922,945 A | 7/1999 | Allmaras et al. | | 73/52 |
| 5,931,786 A | 8/1999 | Whitmore, III et al. | | 600/459 |
| 5,935,339 A | 8/1999 | Henderson et al. | | 134/1 |
| 5,951,476 A | 9/1999 | Beach | | 600/439 |
| 5,976,092 A | 11/1999 | Chinn | | 600/459 |
| 5,993,389 A | 11/1999 | Driscoll, Jr. et al. | | 600/371 |
| 5,997,481 A | 12/1999 | Adams et al. | | 600/459 |
| 6,007,499 A | 12/1999 | Martin et al. | | 601/3 |
| 6,036,650 A | 3/2000 | Wu et al. | | 600/462 |
| 6,039,694 A | 3/2000 | Larson et al. | | 600/459 |
| 6,050,943 A | 4/2000 | Slayton et al. | | 600/439 |
| 6,067,371 A | 5/2000 | Gouge et al. | | 382/128 |
| 6,071,239 A | 6/2000 | Cribbs et al. | | 600/439 |
| 6,128,522 A | 10/2000 | Acker et al. | | 600/411 |
| 6,179,831 B1 | 1/2001 | Bliweis | | 606/21 |
| 6,200,539 B1 | 3/2001 | Sherman et al. | | 422/186.04 |
| 6,221,015 B1 | 4/2001 | Yock | | 600/439 |
| 6,267,734 B1 | 7/2001 | Ishibashi | | 601/2 |
| 6,406,759 B1 | 6/2002 | Roth | | 427/562 |
| 6,409,720 B1 | 6/2002 | Hissong et al. | | 606/27 |
| 6,425,867 B1 | 7/2002 | Vaezy et al. | | 600/439 |
| 6,443,894 B1 | 9/2002 | Sumanaweera et al. | | 600/443 |
| 6,488,639 B1 | 12/2002 | Ribault et al. | | 601/2 |
| 6,491,672 B2 | 12/2002 | Slepian et al. | | 604/267 |
| 6,548,047 B1 | 4/2003 | Unger | | 424/9.51 |
| 6,551,576 B1 | 4/2003 | Unger et al. | | 424/9.52 |
| 6,584,360 B2 | 6/2003 | Francischelli et al. | | 607/98 |
| 6,595,934 B1 | 7/2003 | Hissong et al. | | 601/3 |
| 6,599,256 B1 | 7/2003 | Acker et al. | | 601/2 |
| 6,626,855 B1 | 9/2003 | Weng et al. | | 601/3 |
| 6,633,658 B1 | 10/2003 | Dabney et al. | | 382/128 |
| 6,656,136 B1 | 12/2003 | Weng et al. | | 601/2 |
| 6,676,601 B1 | 1/2004 | Lacoste et al. | | 600/439 |
| 6,685,639 B1 | 2/2004 | Wang et al. | | 600/439 |
| 6,706,892 B1 | 3/2004 | Ezrin et al. | | 548/548 |
| 6,709,407 B2 | 3/2004 | Fatemi | | 600/559 |
| 6,716,184 B2 | 4/2004 | Vaezy et al. | | 601/3 |
| 6,719,694 B2 | 4/2004 | Weng et al. | | 600/439 |
| 6,719,699 B2 | 4/2004 | Smith | | 600/459 |
| 6,726,627 B1 | 4/2004 | Lizzi et al. | | 600/439 |
| 6,735,461 B2 | 5/2004 | Vitek et al. | | 600/411 |
| 6,764,488 B1 | 7/2004 | Burbank et al. | | 606/51 |
| 6,846,291 B2 | 1/2005 | Smith et al. | | 600/459 |
| 6,875,176 B2 | 4/2005 | Mourad et al. | | 600/442 |
| 6,875,420 B1 | 4/2005 | Quay | | 424/9.52 |
| 6,905,498 B2 | 6/2005 | Hooven | | 606/50 |
| 6,932,771 B2 | 8/2005 | Whitmore et al. | | 607/105 |
| 6,955,648 B2 | 10/2005 | Mozayeni et al. | | 600/454 |
| 7,022,077 B2 | 4/2006 | Mourad et al. | | 600/442 |
| 7,052,463 B2 | 5/2006 | Peszynski et al. | | 600/459 |
| 7,149,564 B2 | 12/2006 | Vining et al. | | 600/425 |
| 7,260,250 B2 | 8/2007 | Summers et al. | | 382/128 |
| 7,285,093 B2 | 10/2007 | Anisimov et al. | | 600/437 |
| 7,445,599 B2 | 11/2008 | Kelly et al. | | 600/437 |
| 7,470,241 B2 | 12/2008 | Weng et al. | | 601/3 |
| 7,534,209 B2 | 5/2009 | Abend | | 600/437 |
| 7,684,865 B2 | 3/2010 | Aldrich et al. | | 607/40 |
| 7,697,972 B2 | 4/2010 | Verard et al. | | 600/424 |
| 2002/0016557 A1 | 2/2002 | Duarte et al. | | 601/2 |
| 2002/0193831 A1 | 12/2002 | Smith, III | | 607/5 |
| 2003/0018255 A1 * | 1/2003 | Martin et al. | | 600/437 |
| 2003/0069569 A1 | 4/2003 | Burdette et al. | | 606/27 |
| 2003/0171700 A1 * | 9/2003 | Martin et al. | | 601/2 |
| 2003/0195420 A1 | 10/2003 | Mendlein et al. | | 600/459 |
| 2003/0208101 A1 | 11/2003 | Cecchi | | 600/466 |
| 2004/0002654 A1 | 1/2004 | Davidson et al. | | 600/454 |
| 2004/0078034 A1 | 4/2004 | Acker et al. | | 606/27 |
| 2004/0097840 A1 | 5/2004 | Holmer | | 601/2 |
| 2004/0122493 A1 | 6/2004 | Ishibashi et al. | | 600/437 |
| 2004/0153126 A1 | 8/2004 | Okai | | 606/27 |
| 2004/0234453 A1 | 11/2004 | Smith | | 424/9.5 |
| 2004/0254620 A1 | 12/2004 | Lacoste et al. | | 607/96 |
| 2005/0065436 A1 | 3/2005 | Ho et al. | | 600/431 |
| 2005/0182319 A1 | 8/2005 | Glossop | | 600/424 |
| 2005/0240102 A1 | 10/2005 | Rachlin et al. | | 600/437 |
| 2006/0184069 A1 | 8/2006 | Vaitekunas | | 601/2 |
| 2006/0264832 A1 * | 11/2006 | Skwarek et al. | | 604/151 |
| 2008/0045864 A1 | 2/2008 | Candy et al. | | 601/2 |
| 2008/0045865 A1 | 2/2008 | Kislev | | 601/3 |
| 2008/0200815 A1 | 8/2008 | Van Der Steen et al. | | 600/467 |
| 2008/0319375 A1 | 12/2008 | Hardy | | 604/22 |

FOREIGN PATENT DOCUMENTS

| | | |
|---|---|---|
| EP | 1 265 223 | 12/2002 |
| JP | H09-103434 | 4/1997 |
| JP | 2002-500939 | 1/2002 |
| JP | 2004-113789 | 4/2004 |
| WO | WO 97/31364 | 8/1997 |
| WO | WO 00/72919 | 12/2000 |
| WO | WO 02/069805 | 9/2002 |

OTHER PUBLICATIONS

Chao, Min-Kang, Sheng-Wen Cheng. "Aspheric lens design" Ultrasonics Symposium, 2000 IEEE, vol. 2, pp. 1025-1028, Oct. 2000.
Hadimioglu, B., E.G. Rawson, R. Lujan, M. Lim, J.C. Zesch, B.T. Khuri-Yakub, and C.F. Quate. "High-Efficiency Fresnel Acoustic Lenses" Ultrasonics Symposium, 1993 IEEE, pp. 579-582.
Lalonde, R.J., A. Worthington, and J.W. Hunt. "Field conjugate acoustic lenses for ultrasound hyperthermia" Ultrasonics, Ferroelectrics and Frequency Control, IEEE Transactions, vol. 40, Issue 5, pp. 592-602, Sep. 1993.
Aaslid et al., "Noninvasive transcranial Doppler ultrasound recording of flow velocity in basal cerebral arteries." *Journal of Neurosurgery*, vol. 57: 769-774, 1982.
Campbell et al. "Pulsatile Echo-encephalography." *Acta Neurologica Scandinavica Supplementum 45*, vol. 46: 1-57, 1970.
Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.
Gao et al., "Imaging of the Elastic Properties of Tissue—A Review." *Ultrasound in Medicine & Biology*, vol. 22, No. 8: 959-977, 1996.
Klingelhöfer et al., "Chapter 4: Functional Ultrasonographic Imaging" In Babikian VL, Wechsler LR, eds. *Transcranial Doppler Ultrasonography*. Woburn, MA: Butterworth-Heinemann, 49-66, 1999.
Markwalder et al., "Dependency of Blood Flow Velocity in the Middle Cerebral Artery on End-Tidal Carbon Dioxide Partial Pressure—A Transcranial Ultrasound Doppler Study." *Journal of Cerebral Blood Flow and Metabolism*, vol. 4, No. 3: 368-372, 1984.
Anand et al., "Using the ATL 1000 to Collect Domodulated RF Data for Monitoring HIFU Lesion Formation." *Presented at SPIE Medical Imaging* 2003. 1lpp, 2003.
Bauer et al., "Ultrasound Imaging with SonoVue: Low Mechanical Index Real-Time Imaging." *Acad. Radiol.*; vol. 9, Suppl. 2: S282-S284, 2002.
Chong et al., "Tissue Factor and Thrombin Mediate Myocardial Ischemia-Reperfusion Injury." *The Society of Thoracic Surgeons*, vol. 75: S649-655, 2003.
Ganapathy et al., "A New General Triangulation Method for Planar Contours." *Computer Graphics* vol. 16, No. 3:69-75, 1982.
Guzman et al., "Ultrasound-Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.
Iannuzzi et al., "Ultrasonographic Correlates of Carotid Atherosclerosis in Transient Ischemic Attack and Stroke." *Stroke*, ProQuest Medical Library, vol. 26, No. 4: 614-619, 1995.
Idell et al., "Fibrin Turnover in Lung Inflammation and Neoplasia." *American Journal of Respiratory and Critical Care Medicine*, vol. 163: 578-584, 2001.
Indman, Paul. "Alternatives in Gynecology." *Hysteroscopy*, OBGYN.net, 2000. http://www.gynalternatives.com/hsc.html.
Kaczkowski et al., "Development of a High Intensity Focused Ultrasound System for Image-Guided Ultrasonic Surgery." *Ultrasound for Surgery*, 2001. <http://cimu.apl.washington.edu/hifusurgerysystem.html>.
Kang et al., "Analysis of the Measurement Precision of Arterial Lumen and Wall Areas Using High-Resolution MRI." *Magnetic Resonance in Medicine*, vol. 44: 968-972, 2000.
Klibanov et al., "Detection of Individual Microbubbles of an Ultrasound contrast Agent: Fundamental and Pulse Inversion Imaging." *Academy of Radiology*, vol. 9, Suppl. 2: S279-S281, 2002.
Kudo et al., "Study on Mechanism of Cell Damage Caused by Microbubbles Exposed to Ultrasound" *Ultrasound in Medicine & Biology*, vol. 29, Supplement: 4pp, 2003.
Meyers, D. "Multiresolution tiling." *Computer Graphics*, No. 5: 325-340, 1994.
Miller et al., "A Review of In Vitro Bioeffects of Inertial Ultrasonic Cavitation From a Mechanistic Perspective." *Ultrasound in Medicine & Biology*, vol. 22, No. 9: 1131-1154, 1996.

Miller et al., "Diagnostic ultrasound activation of contrast agent gas bodies induces capillary rupture in mice." *PNAS*, vol. 97, No. 18: 10179-10184, 2000.
Ng et al., "Therapeutic Ultrasound: Its Application in Drug Delivery." *Medicinal Research Reviews*, vol. 22, No. 2: 204-233, 2002.
O'Leary et al., "Carotid-artery Intima and Media Thickness as a Risk Factor for Myocardial Infarction and Stroke in Older Adults." Cardiovascular Health Study Collaborative Research Group. *New England Journal of Medicine*, vol. 340, No. 1: 14-22, Jan. 7, 1999.
Ostensen et al., "Characterization and Use of Ultrasound Contrast Agents." *Academy of Radiology*, vol. 9, Suppl. 2: S276-S278, 2002.
Owaki et al., "The Ultrasonic Coagulating and Cutting System Injuries Nerve Function." *Endoscopy*, vol. 34, No. 7: 575-579, 2002.
Pignoli et al., "Intimal plus medial thickness of the arterial wall: a direct measurement with ultrasound imaging." *Circulation*, vol. 74, No. 6:1399-1406, Dec. 1986.
Poliachik et al., "Activation, Aggregation and Adhesion of Platelets Exposed to High-Intensity Focused Ultrasound." *Ultrasound in Medicine & Biology*, vol. 27, No. 11: 1567-1576, 2001.
Poliachik et al., "Effect of High-Intensity Focused Ultrasound on Whole Blood With or Without Microbubble Contrast Agent." *Ultrasound in Medicine & Biology*, vol. 25, No. 6: 991-998, 1999.
Porter et al., "Ultrasound, Microbubbles and Thrombolysis." *Progress in Cardiovascular Diseases*, vol. 44, No. 2: 101-110, Oct. 2001.
Rivens et al., "Vascular Occlusion Using Focused Ultrasound Surgery for Use in Fetal Medicine." *European Journal of Ultrasound*, vol. 9: 89-97, 1999.
Rosen et al., "Vascular Occlusive Diseases." 37pp., revised 2002.
Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.
Rosenschein et al., "Ultrasound Imaging—Guided Nonivasive Ultrasound Thrombolysis—Preclinical Results." *Circulation*, vol. 102: 238-245, 2000. <http://www.circulationaha.com.org>.
Schulte-Altedorneburg et al., "Accuracy of in Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.
Tachibana et al., "Albumin Microbubble Echo-Contrast Material as an Enhancer for Ultrasound Accelerated Thrombolysis." *Circulation*, vol. 92: 1148-1150, 1995.
Tachibana et al., "The Use of Ultrasound for Drug Delivery." *Echocardiography*, vol. 18, No. 4: 323-328, May 2001.
Tardy et al., "In Vivo Ultrasound Imaging of Thrombi Using a Target-specific Contrast Agent." *Academy of Radiology*, vol. 9, Suppl. 2: S294-S296, 2002.
Vaezy et al., "Acoustic surgery." *Physics World*: 35-39, Aug. 2001.
Vaezy et al., "Hemostasis and Tumor Treatment using High Intensity Focused Ultrasound: Experimental Investigations and Device Development." *First International Workship on the Application of HIFU in Medicine*: 46-49, 2001.
Vaezy et al., "Hemostatsis using high intensity focused ultrasound." *European Journal of Ultrasound*, vol. 9: 79-87, 1999.
Vaezy et al., "Intra-operative acoustic hemostasis of liver: production of a homogenate for effective treatment." *Ultrasonics*, vol. 43: 265-269, 2005.
Von Land et al., "Development of an Improved Centerline Wall Motion Model." *IEEE*: 687-690, 1991.
Watkin et al., "Multi-Modal Contrast Agents: A First Step." *Academy of Radiology*, vol. 9, Suppl. 2: S285-S287, 2002.
Wickline et al., "Blood Contrast Enhancement with a Novel, Non-Gaseous Nanoparticle Contrast Agent." *Academy of Radiology*, vol. 9, Suppl. 2: S290-S293, 2002.
Williamson et al., "Color Doppler Ultrasound Imaging of the Eye and Orbit."*Survey of Ophthamology*, vol. 40, No. 4: 255-267, 1996.
Yu et al., "A microbubble agent improves the therapeutic efficiency of high intensity focused ultrasound: a rabbit kidney study." *Urological Research*, PubMed: Abstract, 2004
n.a., "Cavitation." Ultrasound TIP—U.S. Database: Dec. 12, 2007.
n.a., "Mechanical Bioeffects in the Presence of Gas-Carrier Ultrasound Contrast Agents." *Journal of Ultrasound & Medicine*, vol. 19: 120-142, 2000.

n.a., "Breast Cancer—Insightec: focused ultrasound for non invasive treatment." FAQ, 2000. <http://www.exablate2000.com/physicians_faq.html>.

Accord et al., "The Issue of Transmurality in Surgical Ablation for Atrial Fibrillation." *Cardiothoracic Surgery Network*: 3pp, Aug. 8, 2005.

Amenta et al., "A New Voronoi-Based Surface Reconstruction Algorithm." *Computer Graphics*: 7pp, 1998.

American Red Cross., "Blood 101." 4pp., Dec. 11, 2007.

Anand et al., "Monitoring formation of high intensity focused ultrasound (HIFU) induced lesions using backscattered ultrasound." *Acoustical Society of America*; Mar. 10, 2004.

Anand et al., "Using the ATL 1000 to Collect Domodulated RF Data for Monitoring HIFU Lesion Formation." *Presented at SPIE Medical Imaging 2003*. 11pp, 2003.

Aurenhammer, F. "Voronoi diagrams—A Survey of a Fundamental Geometric Data Structure." *ACM Computing Surveys*, vol. 23, No. 3: 345-405, Sep. 1991.

Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.

Bauer et al., "Ultrasound Imaging with SonoVue: Low Mechanical Index Real- Time Imaging." *Acad. Radiol.*; vol. 9, Suppl. 2: S282-S284, 2002.

Bokarewa et al., "Tissue factor as a proinflammatory agent." *Arthritis Research*, vol. 4: 190-195, Jan. 10, 2002.

Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.

Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.

Buller et al., "Accurate Three-dimensional Wall Thickness Measurement From Multi-Slice Short-Axis MR Imaging." *Computers in Cardiology*, 245-248, 1995.

Cheliue et al., "Fabrication of Medical Models From Scan Data via Rapid Prototyping Techniques." 9 pp., Feb. 7, 2007.

Chen et al., "A comparison of the fragmentation thresholds and inertial cavitation doses of different ultrasound contrast agents." *Journal of the Acoustical Society of America*, vol. 113, No. 1: 643-665, Jan. 2003.

Chen et al., "Inertial Cavitation Dose and Hemolysis Produced In Vitro With or Without Optison." *Ultrasound in Medicine & Biology*, vol. 29, No. 5: 725-737, 2003.

Chong et al., "Tissue Factor and Thrombin Mediate Myocardial Ischemia- Reperfusion Injury." *The Society of Thoracic Surgeons*, vol. 75: S649-655, 2003.

Dayton et al., "The magnitude of radiation force on ultrasound contrast agents." *Journal of the Acoustical Society of America*, vol. 112, No. 5, Part 1: 2183-2192, Nov. 2002.

Dempsey et al., "Thickness of Carotid Artery Atherosclerotic Plaque and Ischemic Risk." *Neurosurgery*, vol. 27, No. 3: 343-348, 1990.

Ebbini et al., "Image-guided noninvasive surgery with ultrasound phased arrays." *SPIE*, vol. 3249: 230-239, Apr. 2, 1998.

Edelsbrunner, Herbert. "Geometry and Topology for Mesh Generation." *Cambridge University Press*: 68pp, 2001.

Everbach et al., "Cavitational Mechanisms in Ultrasound-Accelerated Thrombolysis at 1 MHz." *Ultrasound in Medicine & Biology*, vol. 26, No. 7: 1153-1160, 2000.

Ewert et al., "Anti-myeloperoxidase antibodies stimulate neutrophils to damage human endothelial cells." *Kidney International*, vol. 41: 375-383, 1992.

Ganapathy et al., "A New General Triangulation Method for Planar Contours." *Computer Graphics* vol. 16, No. 3:69-75, 1982.

Gray, Henry. "The Skull." *Anatomy of the Human Body*: 7pp., 1918.

Guzman et al., "Ultrasound—Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.

Han et al., "A Fast Minimal Path Active Contour Model." IEEE Transactions on Image Processing, vol. 10, No. 6: 865-873, Jun. 2001.

Hatangadi, Ram. "A Novel Dual Axis Multiplanar Transesophageal Ultrasound Probe for Three-Dimensional Echocardiograph."_*University of Washington, Department of Sciences and Engineering*, vol. 55-11B: Abstract 1pg, 1994.

Holt et al., "Bubbles and Hifu: the Good, the Bad and the Ugly." *Boston University, Department of Aerospace and Mechanical Engineering*: 120-131, 2002.

Hubka et al., "Three-dimensional echocardiographic measurement of left ventricular wall thickness: In vitro and in vivo validation." *Journal of the American Society of Echocardiography*, vol. 15, No. 2: 129-135, 2002.

Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.

Hynynen et al., "Potential Adverse Effects of High-Intensity Focused Ultrasound Exposure on Blood Vessels In Vivo." *Ultrasound in Medicine & Biology*, vol. 22, No. 2: 193-201, 1996.

\* cited by examiner

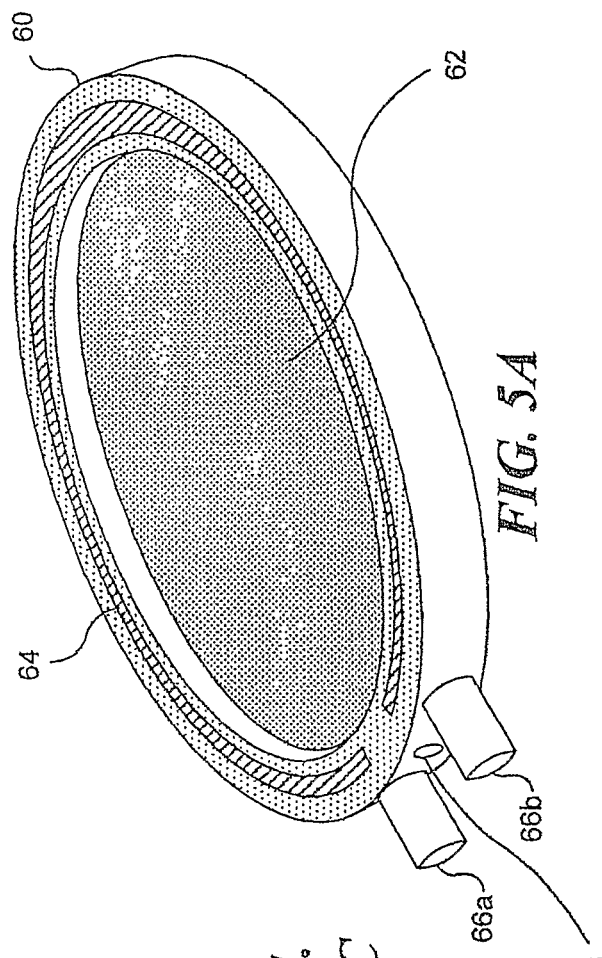
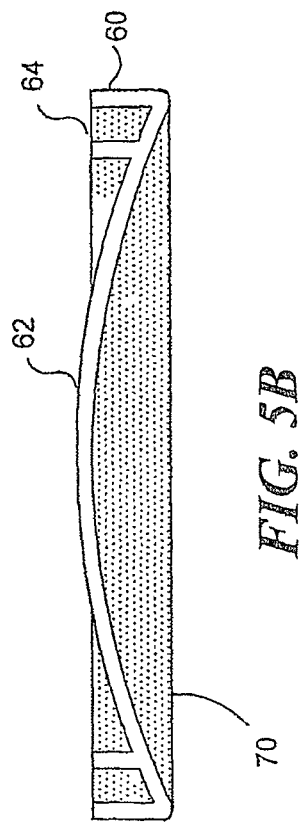
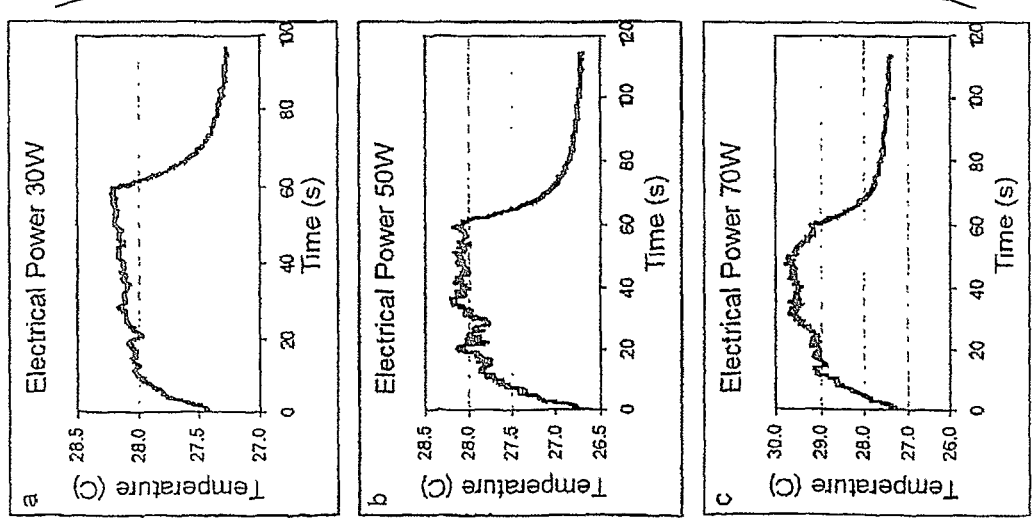
*FIG. 5A*
*FIG. 5B*
*FIGS. 2A-2C*

# THIN-PROFILE THERAPEUTIC ULTRASOUND APPLICATORS

RELATED APPLICATIONS

This application is the U.S. National Stage of International Application No. PCT/US06/36106, filed Sep. 15, 2006 which claims the benefit of U.S. Provisional Application No. 60/718,085, filed on Sep. 16, 2005 and U.S. Provisional Application No. 60/825,610, filed on Sep. 14, 2006.

GOVERNMENT RIGHTS

This invention was made with government support under grant number 5 RO1 EB000292 awarded by the National Institutes of Health and grant number DAMD17-02-2-0014 awarded by a US Army subcontract award through the University of Mississippi National Center for Physical Acoustics. The government has certain rights in the invention.

BACKGROUND

Ultrasound is widely used for imaging a patient's internal structures without risk of exposure to potentially harmful radiation, as may occur when using X-rays for imaging. An ultrasound examination is a safe diagnostic procedure that uses high frequency sound waves to produce an image of the internal structures of a patient's body. Many studies have shown that these sound waves are harmless and may be used with complete safety, even to visualize the fetus in pregnant women, where the use of X-rays would be inappropriate. Furthermore, ultrasound examinations generally require less time than examinations using other imaging techniques, and ultrasound examinations are typically less expensive than examinations using other imaging techniques.

More recently, the use of high intensity focused ultrasound (HIFU) for therapeutic purposes, as opposed to imaging, has received significant attention in the medical community. HIFU therapy employs ultrasound transducers that are capable of delivering 1,000-10,000 W/cm$^2$ to a focal spot, in contrast to diagnostic imaging ultrasound, where intensity levels are usually below 0.1 W/cm$^2$. A portion of the energy from these high intensity sound waves is transferred to a targeted location as thermal energy. The amount of thermal energy thus transferred can be sufficiently intense to cauterize undesired tissue, or to cause necrosis of undesired tissue (by inducing a temperature rise greater than about 70° C.) without actual physical charring of the tissue. Tissue necrosis can also be achieved by mechanical action alone (i.e., by cavitation that results in mechanical disruption of the tissue structure). Further, if the vascular system supplying blood to an internal structure is targeted, HIFU can be used to induce hemostasis. The focal region of this energy transfer can be tightly controlled so as to obtain necrosis of abnormal or undesired tissue in a small target area without damaging adjoining normal tissue. Thus, deep-seated tumors can be destroyed with HIFU without surgical exposure of the tumor site.

An important consideration in any type of ultrasound therapy system is the form factor of the therapy head (i.e., the portion of the system containing the therapy transducer, which is generally positioned proximate the treatment site before providing therapy). The size and shape of the therapy head in which the therapy transducer is mounted varies depending upon the intended treatment site. For example, to facilitate placement of the therapy head within the corresponding body cavities, transrectal and vaginal therapy probes are each typically elongate in shape and narrow in size.

One significant application of therapeutic ultrasound is the use of HIFU for hemostasis applications. The application of HIFU in an intra-operative setting presents challenges due to the limited space available. It would be desirable to provide a therapy probe having a therapy head exhibiting a relatively small form factor. A significant challenge in providing such a design is that therapeutic transducers generally produce a considerable amount of heat, and cooling is required to prevent damage to surrounding tissue or to the therapy head itself. Therapy heads are often encapsulated in a latex balloon filled with water, and the water is circulated to provide the required cooling, as well as to facilitate acoustically coupling the therapy head to target tissue. Unfortunately, such balloons are bulky, and are not well suited to achieving a therapy head having a small form factor. It would thus be desirable to provide a therapy probe having a therapy head exhibiting a relatively small form factor, which can be cooled without requiring the use of a bulky balloon.

SUMMARY

The concepts disclosed herein encompass apparatus and method for providing therapeutic ultrasound, using a therapy probe having a relatively thin-profile, where the therapy head of the therapy probe incorporates integral fluid channels about the periphery of the therapy head, to enable the highly energetic ultrasound transducer to be cooled during therapy.

A first aspect of these concepts is an ultrasound therapy probe including a therapy head and a generally elongate handle a generally elongate coupled to the therapy head, the generally elongate handle enabling a clinician to manually manipulate and selectively position the therapy head proximate a treatment site. The therapy head includes an ultrasound transducer configured to generate therapeutic ultrasound when energized, and a housing including an inner volume in which the ultrasound transducer is disposed. The housing is configured to support and encompass the ultrasound transducer, and includes a fluid channel disposed about a periphery of at least a portion of the housing. The fluid channel is configured to enable a cooling fluid to be circulated within the fluid channel, to provide cooling of the ultrasound transducer that is disposed in the inner volume. Significantly, this design enables a therapy head with a relatively thin-profile to be achieved, without sacrificing cooling ability. Because transducers suitable for providing therapeutic ultrasound generate significant heat, cooling such transducers is critical. Encapsulating a therapy head in a latex balloon, and circulating a cooling fluid throughout the latex balloon can accomplish cooling, but does not achieve a thin-profile device. As noted above, achieving a thin-profile device has significant advantages for therapeutic procedures implemented in confined spaces or body cavities.

In at least one exemplary embodiment, the inner volume of the head is larger than the ultrasound transducer in order to achieve an air-backed transducer configuration. That is, a rear surface of the transducer (where the therapeutic ultrasound propagates outwardly and away from a front surface of the ultrasound transducer) is disposed immediately adjacent to a volume of air. Such an air-backed configuration complicates the matter of providing adequate cooling to the ultrasound transducer, because the cooling fluid cannot simply be circulated over a rear surface of the ultrasound transducer. Thus, positioning the cooling channels about the periphery of the housing enables a relatively thin-profile air-backed transducer configuration to be achieved, while still maintaining the required cooling. Empirical devices as thin as 1 cm have been built. Although not intended to be limiting on this concept, housing dimensions of one exemplary embodiment are about 4 centimeters in diameter and about 1 centimeter in thickness, for use with an ultrasound transducer having a focal length of about 3.5 centimeters.

In some exemplary embodiments, a curved outer surface of the housing adjacent to the inner volume functions as an acoustic lens, configured to focus an acoustic beam emitted from the ultrasound transducer toward a treatment site, when the ultrasound transducer is energized.

In at least one exemplary embodiment, the housing comprises aluminum. Aluminum exhibits good thermal transfer properties, facilitating cooling of the transducer, and aluminum also exhibits desirable properties with respect to the transmission and focusing of ultrasound waves. It should be recognized however, that aluminum represents only an exemplary material, and the use of aluminum in the housing is not intended to limit the scope of this disclosure. Other materials providing acceptable heat transfer properties, acceptable structural integrity, and acceptable transmission properties with respect to ultrasound waves can also be employed. Specifically, other metals, and plastics can be employed, so long as they exhibit the desired mechanical, structural, and acoustical properties. It should also be recognized that housings can be constructed or fabricated from more than one material, to enable beneficial material properties to be implemented based on specific functions that are carried out by a material. For example, a first material exhibiting good heat transfer properties can be used to implement the cooling fluid channel, and a second material exhibiting good acoustic properties can be used for an acoustic lens, in embodiments in which an acoustic lens is included. Generally, housings should be made of a nontoxic material, and it may be desirable to employ a material that can be easily sterilized.

In some exemplary embodiments, the housing is generally spoon-shaped, a surface of the housing being generally concave. Where the ultrasound transducer is implemented using a concave transducer element, the inner volume is configured with an appropriately shaped surface with which to receive and contact the concave transducer element. Where the ultrasound transducer is implemented using a flat transducer element, the inner volume is configured to receive the flat transducer element. In exemplary embodiments including a concave transducer element and correspondingly curved housing, a thickness at about a center of the portion of the housing separating the ultrasound transducer from a target area can be about ¾ of a wavelength of the ultrasound produced by the ultrasound transducer when energized (or any other odd multiple of ¼ wavelength, i.e., 5/4, 7/4, 9/4, etc.). In exemplary embodiments including a flat transducer element and an acoustic lens, at about a center of the acoustic lens portion of the housing, a distance between the ultrasound transducer and a target area can be equal to about a full wavelength of the ultrasound produced by the ultrasound transducer when energized.

The inner wall of the fluid channel separating the fluid channel from the inner volume can incorporate a plurality of grooves, where the grooves increase a surface area of the inner wall to enhance cooling of the ultrasound transducer that is disposed within the inner volume.

In at least one embodiment, no handle is attached to the therapy head. Instead, a clinician simply grasps the therapy head itself, and moves the therapy head to the treatment site. A strap can be added to secure the therapy head to the clinician's hand.

Yet another aspect of the concepts disclosed herein is directed to an exemplary method for providing ultrasound therapy. The method includes the steps of positioning a therapy probe proximate a treatment site, energizing an ultrasound transducer disposed in the therapy probe to deliver therapeutic ultrasound to the treatment site, and cooling the ultrasound transducer by circulating a cooling fluid about a periphery of at least a portion of a housing of the therapy probe in which the ultrasound transducer is disposed. The method enables a therapy probe having a relatively low-profile therapy head to be achieved, where the therapy head provides cooling sufficient to enable a highly energetic therapy transducer to be employed.

In at least one exemplary embodiment, the housing of the therapy probe includes an inner volume configured to support and encompass the ultrasound transducer, and a fluid channel that extends about at least a portion of the periphery of the inner volume, such that the step of cooling the ultrasound transducer includes the step of circulating the cooling fluid in the fluid channel within the housing. In this embodiment, the fluid channel is disposed between the inner volume and an outer surface of the housing.

The method also can include the step of focusing the therapeutic ultrasound with an acoustic lens that is part of the housing.

Still another aspect of the concepts disclosed herein relates to an exemplary method for physically attaching an ultrasound transducer to a housing, such that a minimum amount of bubbles exist in an adhesive layer used to adhesively couple the ultrasound transducer to the housing.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A schematically illustrates a water pillow for use with an exemplary thin-profile HIFU therapy probe, to provide both acoustic coupling and cooling;

FIG. 1B schematically illustrates an exemplary thin-profile HIFU applicator, including a therapy head and handle;

FIG. 1C schematically illustrates the water pillow of FIG. 1A attached to HIFU applicator of FIG. 1B;

FIGS. 2A-2C graphically demonstrate the effectiveness of the water pillow cooling at different power settings;

Figure 3A:
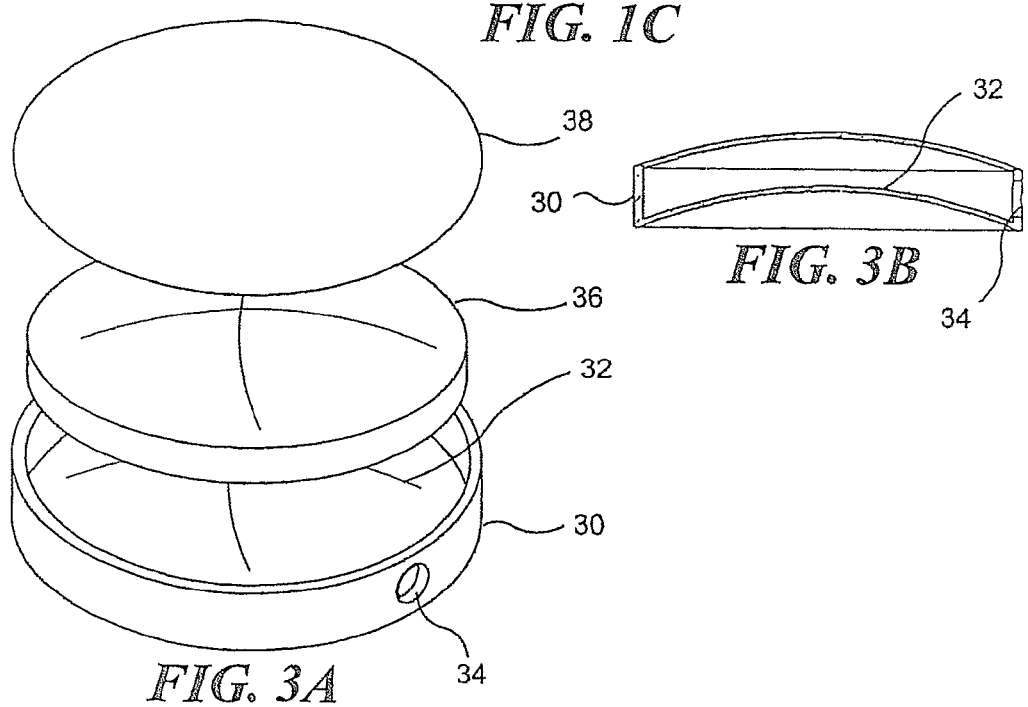
FIG. 3A is an exploded schematic view of an aluminum housing, a concave PZT therapy transducer, and a cover plate employed to provide an exemplary therapy head for a thin-profile HIFU applicator.
Figures 4A, 4B, 4C, 4D, 4E:
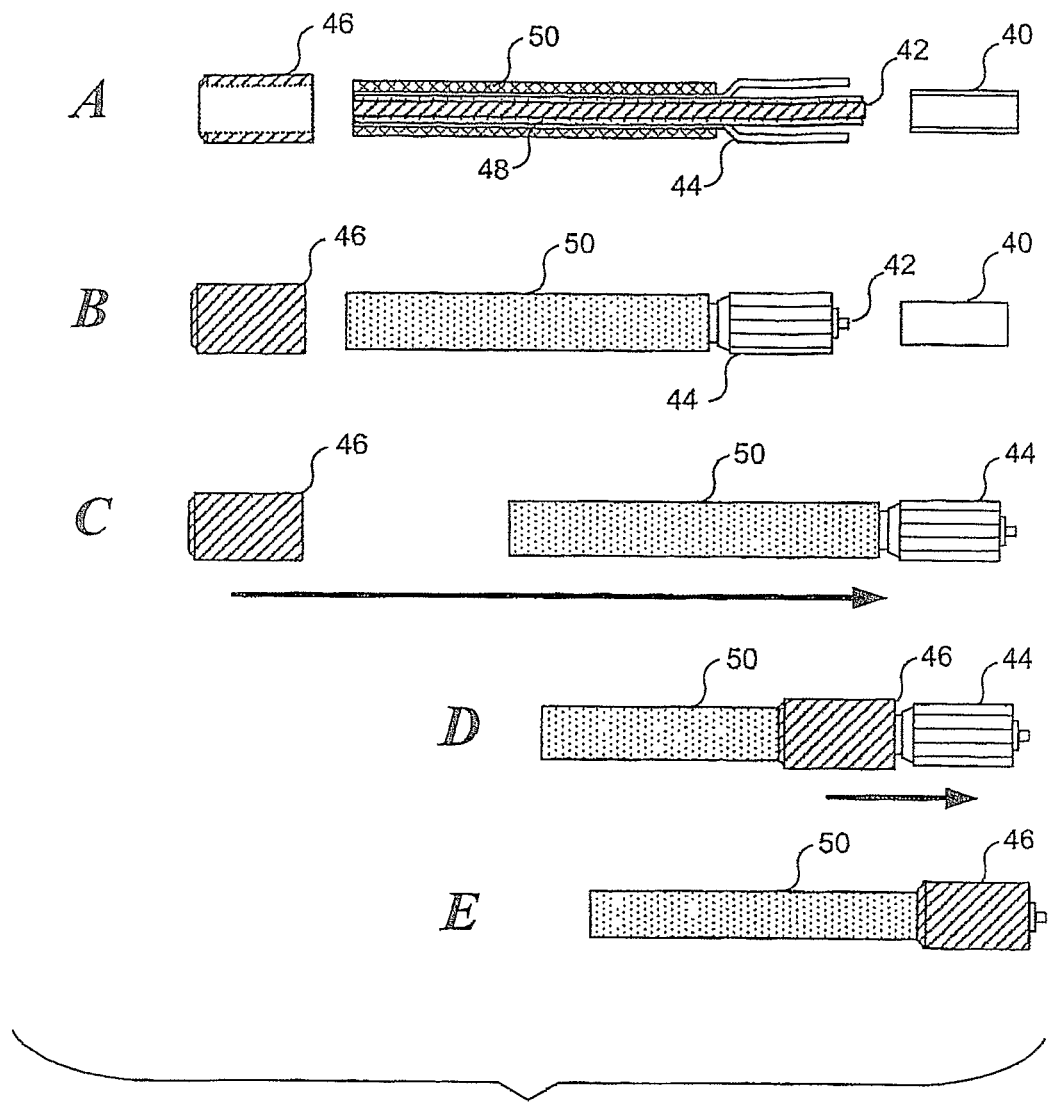
Figure 4F:
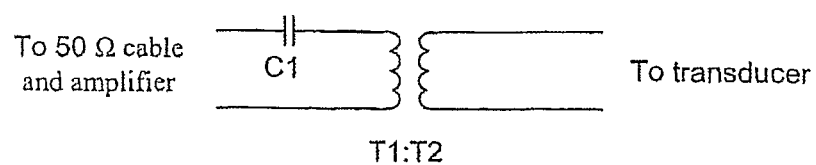
Figure 6:
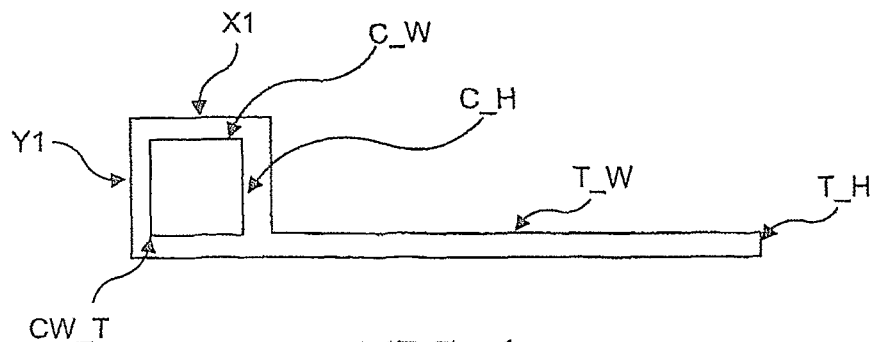
Figure 7A:
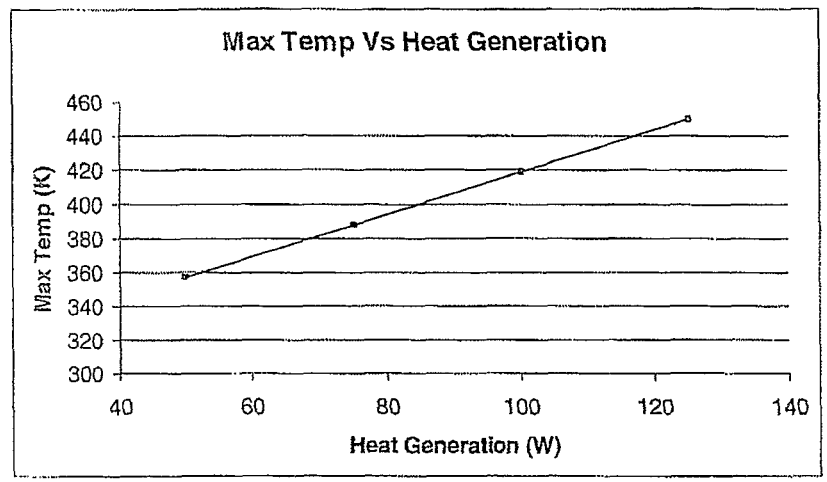
Figure 7B:
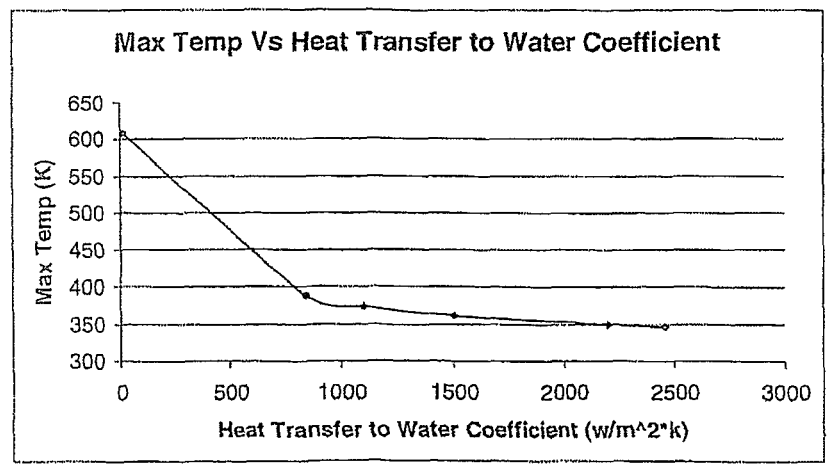
Figure 7C:
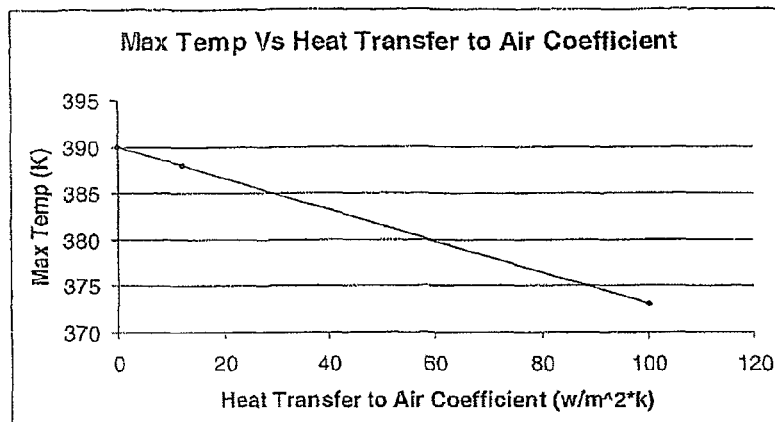
Figure 7D:
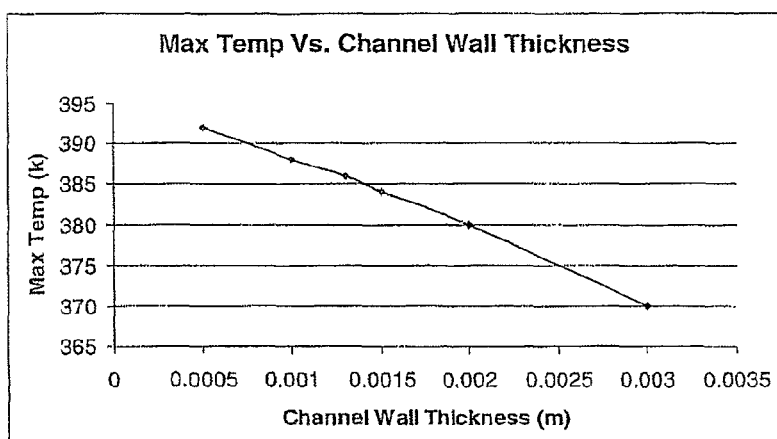
Figure 7E:
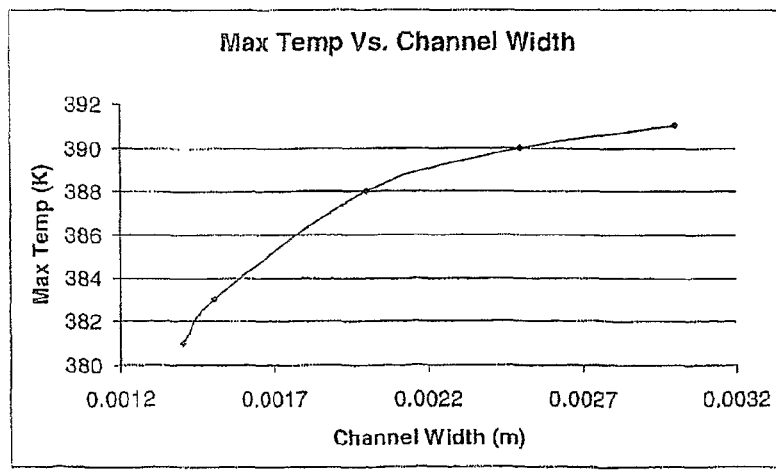
Figure 7F:
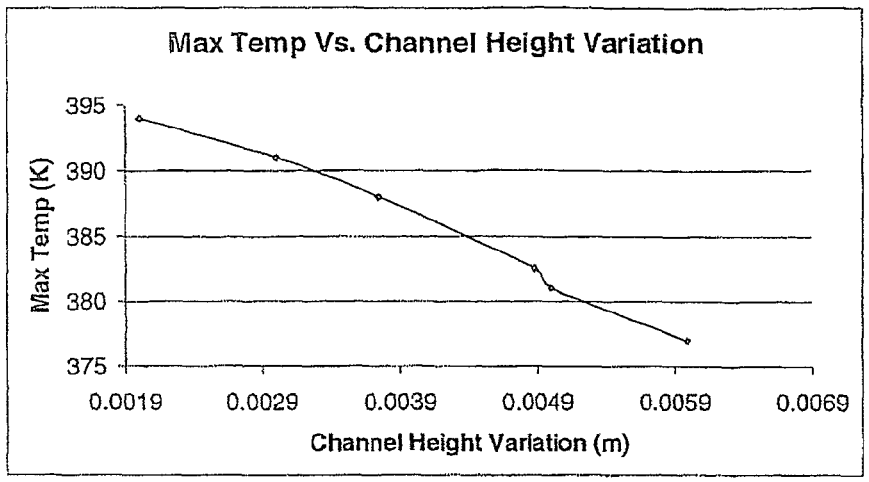
Figure 7G:
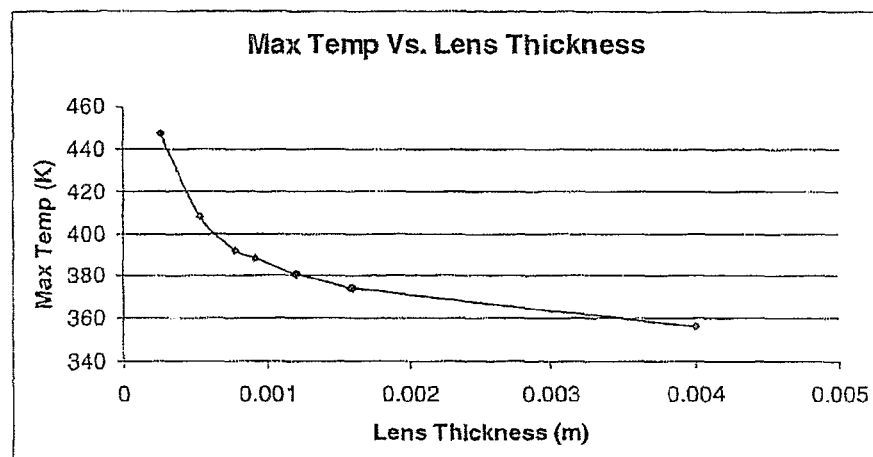
Figure 7H:
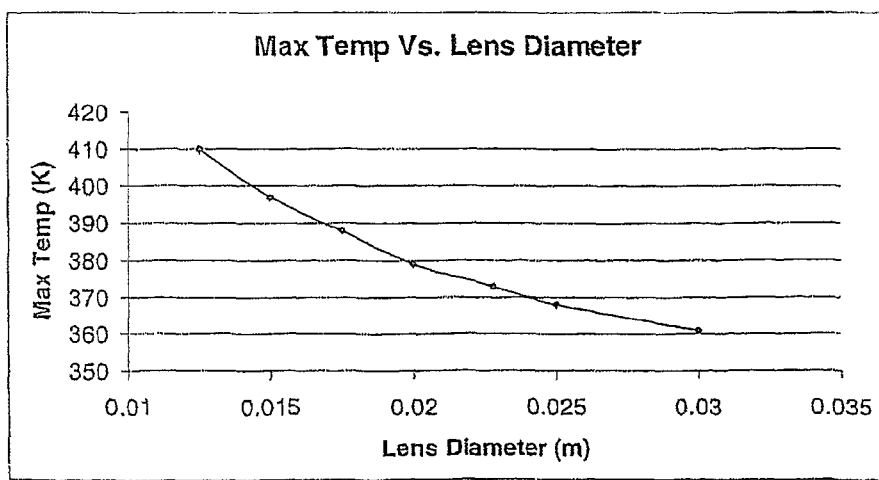
Figure 8A:
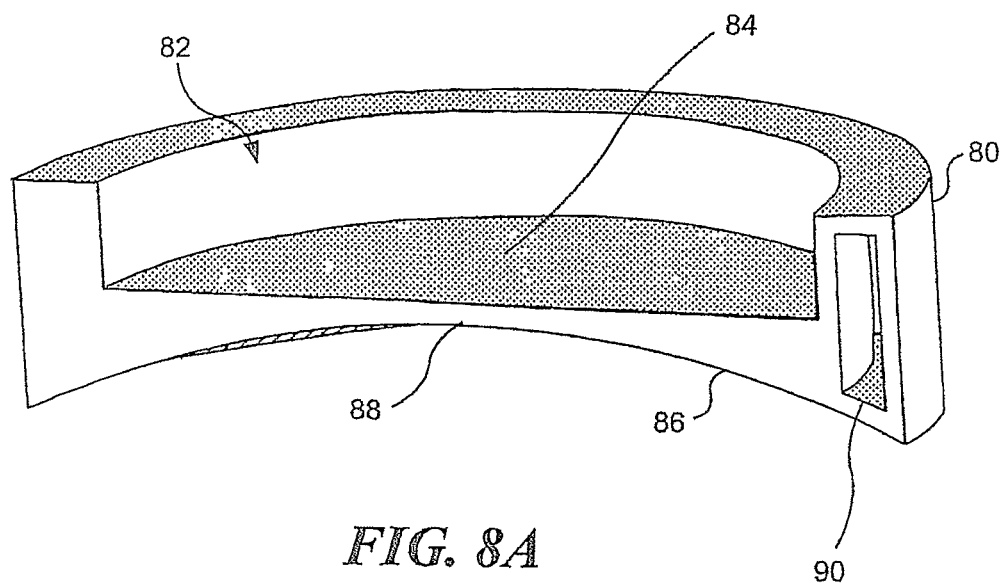
Figure 8B:
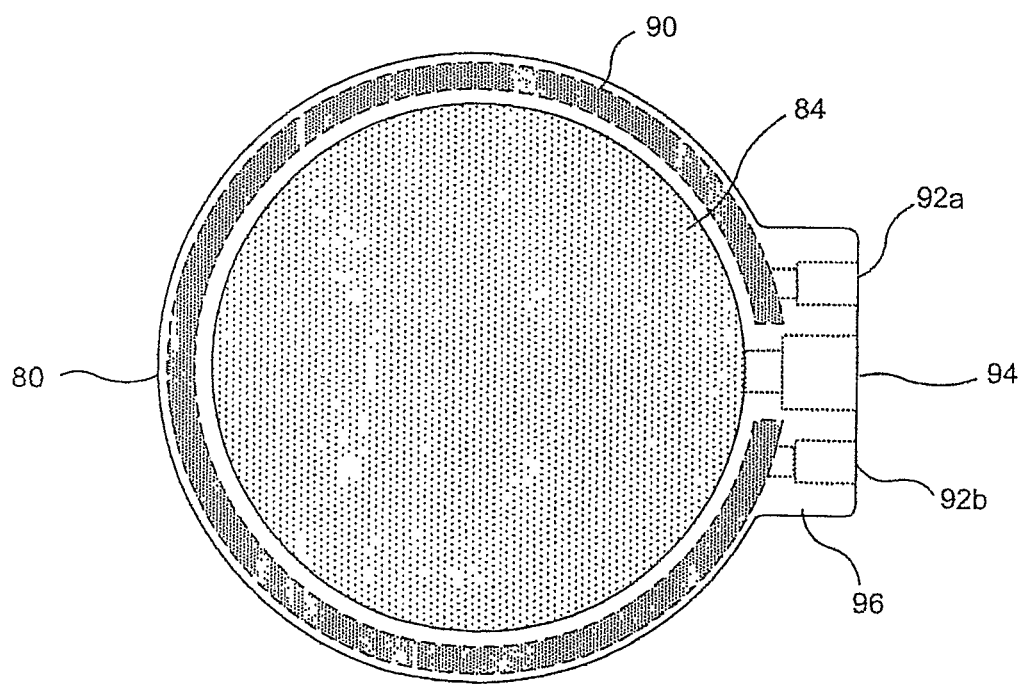
Figure 9:
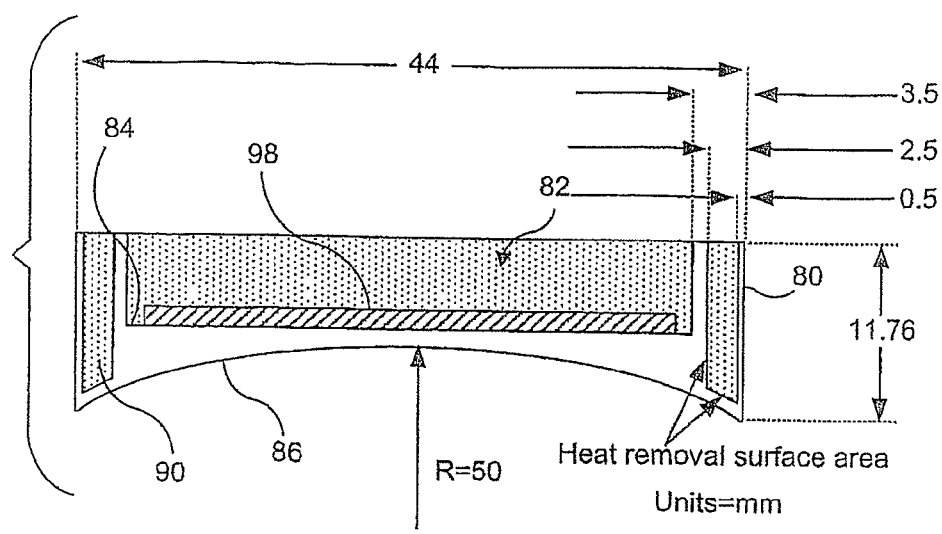
Figure 10A:
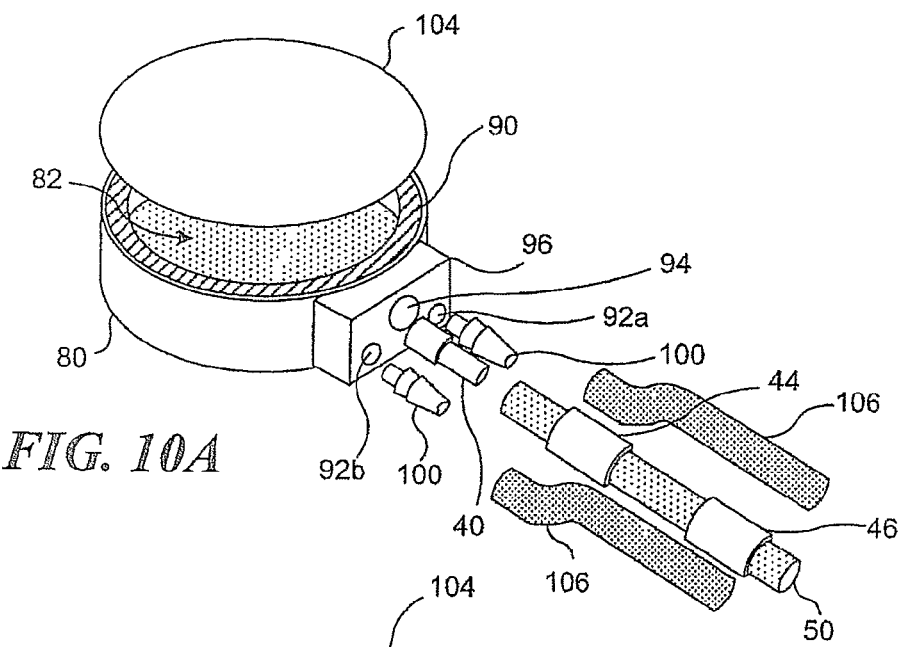
Figure 10B:
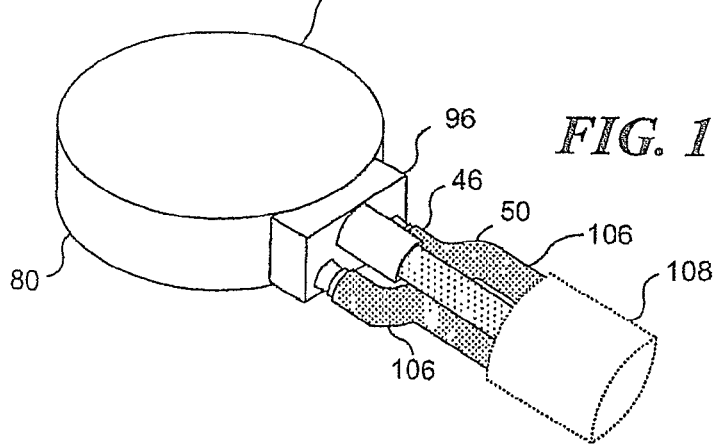
Figure 11A:
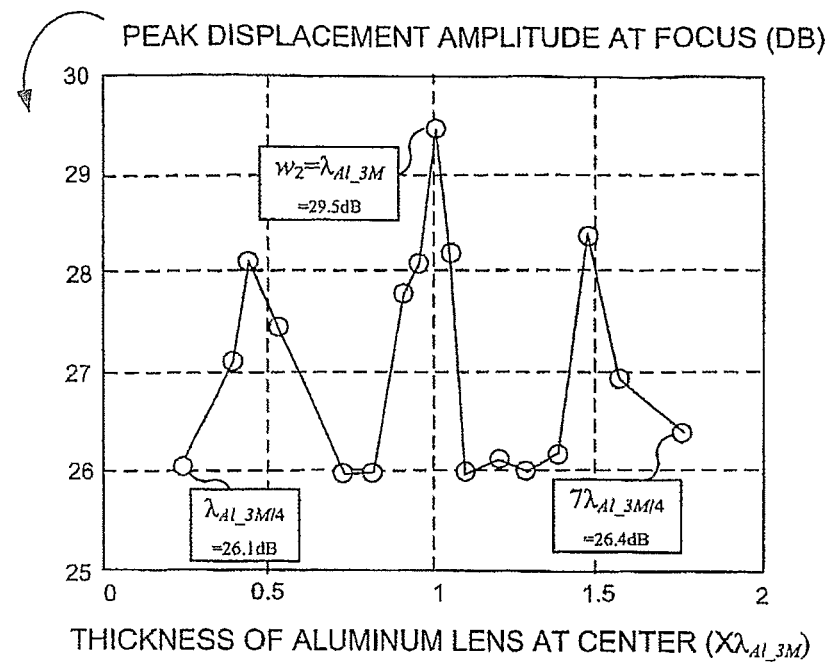
Figure 11B:
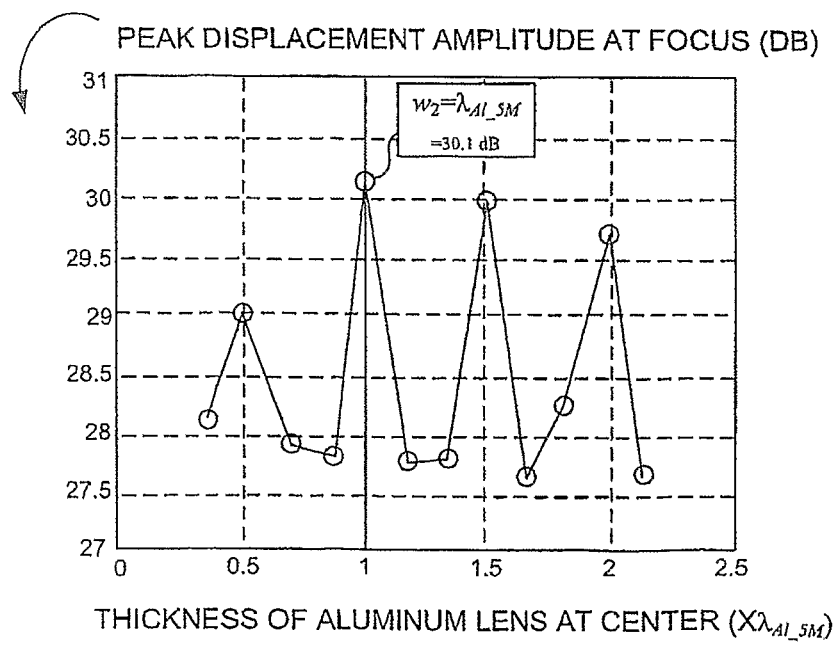
Figure 12A:
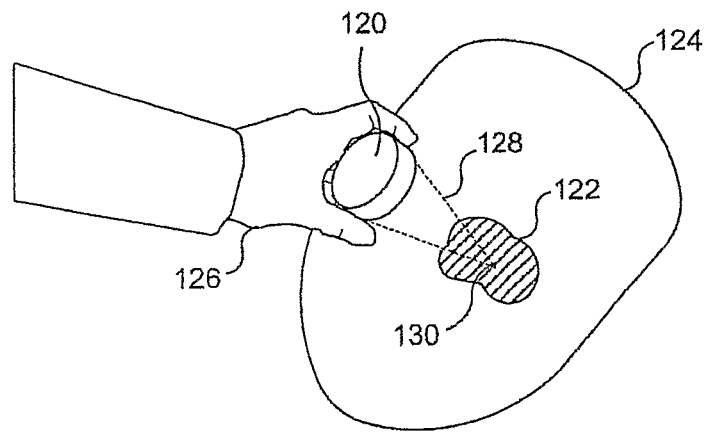
Figure 12B:
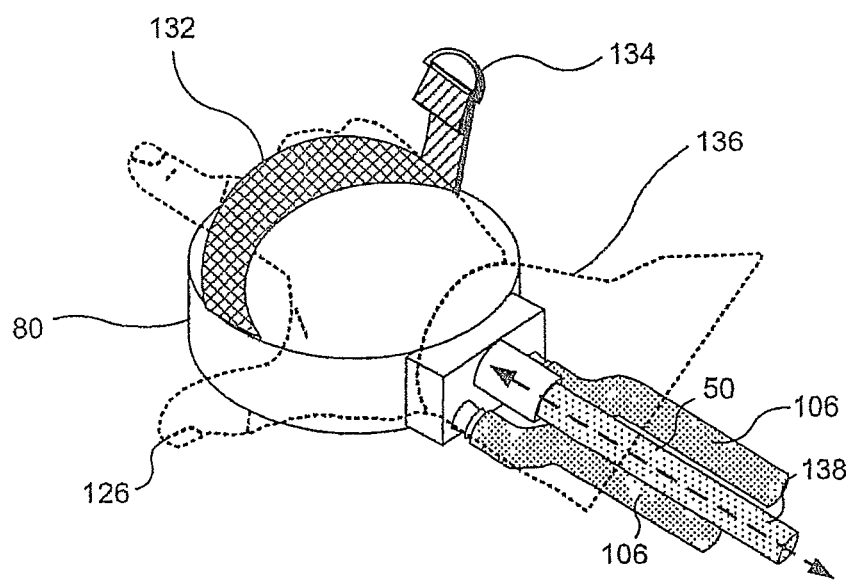

FIG. 4A schematically illustrates a cross-section of a coaxial cable and additional components employed to electrically couple the therapy transducer of FIG. 3A to a power source;

FIG. 4B schematically illustrates an inner conductor being inserted through a crimp splice cap;

FIG. 4C schematically illustrates inner insulation and the inner conductor being inserted into an aluminum tubular fitting, with an outer grounding conductor wrapped around the aluminum tubular fitting;

FIG. 4D schematically illustrates the crimp splice cap being slid along the coaxial cable and around the outer grounding conductor;

FIG. 4E schematically illustrates the crimp splice cap being crimped to the tubular fitting and the outer grounding conductor;

FIG. 4F schematically illustrates a matching circuit configured to maximize the transmitted electrical power to empirical thin-profile devices by adjusting the impedance of the devices;

FIG. 5A schematically illustrates a therapy head housing incorporating a fluid channel disposed about the periphery of the housing;

FIG. 5B is a cross-sectional view of the housing of FIG. 5A;

FIG. 6 schematically illustrates a simplified model used to evaluate a housing incorporating a fluid channel disposed about the periphery of the housing;

FIGS. 7A-7H graphically illustrate the results from the series of simulations based on the model of FIG. 6;

FIG. 8A is a cross-sectional isometric view of another exemplary housing for a thin-profile HIFU applicator, specifically configured to support a flat transducer, and also incorporating a peripheral fluid channel;

FIG. 8B is a plan view of the housing of FIG. 8A;

FIG. 9 is a side view of the housing of FIG. 8A, showing exemplary dimensions in millimeters;

FIG. 10A is an exploded isometric view of a thin-profile HIFU therapy head incorporating the housing of FIG. 8A;

FIG. 10B is an assembled isometric view of the thin-profile HIFU therapy head of FIG. 10A;

FIGS. 11A and 11B graphically illustrate an optimal center thickness for an aluminum acoustic lens; and FIGS. 12A and 12B schematically illustrate an embodiment of a thin-profile HIFU therapy applicator that does not include an elongate handle, such that a clinician simply grasps the therapy head, and directly manipulates the therapy head to selectively position the HIFU focal point.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

The concepts disclosed herein were developed in order to produce a thin-profile HIFU applicator for intra-operative hemostasis. During treatment, the HIFU applicator must be positioned such that the HIFU focus is disposed within or near the injured tissue. The physical size of the HIFU applicator and the limited space available in an intra-operative setting can make accurate placement of the HIFU focus difficult, leading to unnecessary damage to adjacent tissue or the inability to administer treatment. Ideally, surgical HIFU applicators should be light, robust, and have small dimensions that facilitate access to injured tissue.

The terms "therapeutic transducer," "HIFU transducer," and "high intensity transducer," as used herein, all refer to a transducer that is capable of being energized to produce ultrasonic waves that are much more energetic than the ultrasonic pulses produced by an imaging transducer and which can be focused or directed onto a discrete location, such as a treatment site in a target area. Such transducers normally generate more heat during use than ultrasound imaging transducers. Thus, HIFU transducers have a greater need for cooling than do imaging transducers.

As noted above, a challenge in achieving such a thin-profile device is that HIFU transducers generate significant amounts of heat, and therefore require cooling while in operation. Also, in order to achieve higher acoustic power levels, it is important to employ an air-backed transducer configuration. Thus, the rear surface of the transducer must be exposed to a volume of air, and cooling cannot be provided to the rear surface of the transducer by circulating a cooling liquid over it.

The general solution to this problem, encompassed in the concepts disclosed herein, is to provide a water channel disposed around the perimeter of a housing used to provide support for the ultrasound transducer, to convey cooling water, although as discussed below, an initial exemplary design employed a thin-profile external water pillow for cooling. Several empirical studies, discussed below, were performed to optimize the housing design.

Figure 1A:
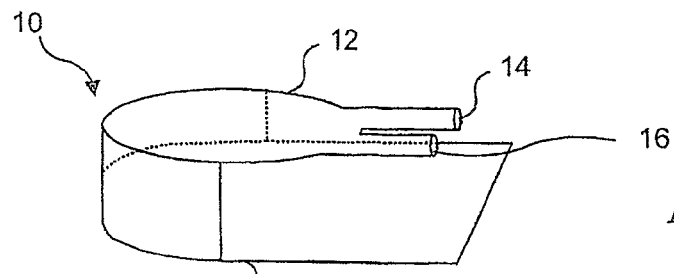
Figure 1B:
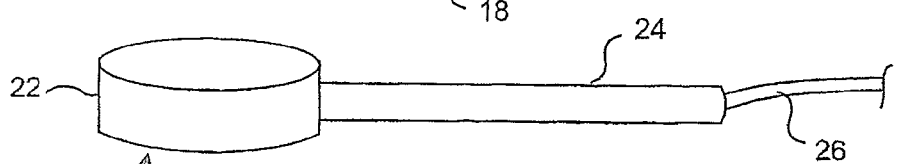
Figure 1C:
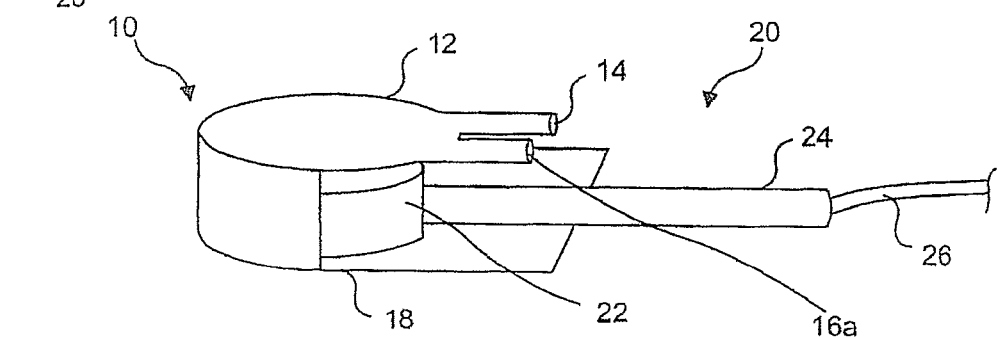

Many prior art designs have employed a cooling fluid chamber that is coupled to a front surface of the transducer, so that the cooling fluid also acts as an acoustic coupling between the transducer and a mass of tissue. Most often, the conventional therapy head containing the transducer has been encapsulated in a latex balloon, and cooling fluid is circulated through the latex balloon. Significantly, prior art latex balloon/expandable member configurations were not designed for and were not appropriate for low-profile applications. FIGS. 1A-1C schematically illustrate a thin-profile HIFU therapy probe and a relatively thin-profile external cooling pillow, which together can be employed to achieve a thin-profile HIFU therapy probe.

FIG. 1A schematically illustrates an acoustic coupler configured to be attached to a thin-profile HIFU therapy probe. Acoustic coupler 10 includes a liquid chamber 12, a liquid inlet 14, a liquid outlet 16, and a pouch 18. Pouch 18 defines an open-ended volume configured to receive the head of a HIFU therapy probe. FIG. 1B schematically illustrates an exemplary acoustic device 20 including a therapy head 22, a handle 24, and a lead 26 that couples the transducer to a power supply (not shown). Therapy head 22 includes a HIFU therapy transducer (not separately shown). FIG. 1C schematically illustrates acoustic coupler 10 of FIG. 1A attached to acoustic device 20 of FIG. 1B. Note that therapy head 22 is substantially encompassed by the open-ended volume of pouch 18. Acoustic coupler 10 is configured to conform to the therapy head in this embodiment and further includes a surface configured to conform to an adjacent surface of a physical mass (not shown) into which acoustic energy from the transducer is to be directed. Preferably, pouch 18 has dimensions selected to accommodate the form factor of therapy head 22, so that an interference fit is achieved when therapy head 22 is introduced into pouch 18.

FIGS. 2A-2C graphically demonstrate the effectiveness of the water pillow cooling at different power settings.

A first empirical implementation of thin-profile acoustic device 20 included an air-backed concave lead-zirconate-titanate (PZT-4) element encased in a spoon-shaped aluminum housing having a diameter of about 4 cm and a thickness of about 1 cm. The housing front surface had a thickness of about ¾ of an ultrasound wavelength (i.e., about 0.92 mm in aluminum) to provide acoustic matching. The device exhibited a resonant frequency of 6.26 MHz, and an efficiency of about 42%. The ultrasound field was observed using hydrophone field mapping and radiation force balance. The full-width half-maximum (FWHM) dimensions of the focal region were about 0.6 mm and 2.2 mm in lateral and axial dimensions, respectively. The maximal intensity at the focus was 9,500 W/cm$^2$ (in water). The device was tested using a BSA-polyacrylamide gel phantom and a rabbit kidney in vivo. HIFU application for ten seconds produced lesions in the gel phantom, i.e., a lesion width of 3 mm, and for the rabbit kidney in vivo specimen, a lesion width of 8 mm. Such a thin-profile HIFU applicator has the advantages of high efficiency, simple design, and small dimensions.

The PZT element employed in the first empirical device was a concave element having a focal length of 3.5 cm, and a resonant frequency of 5.2 MHz. The PZT element was mounted in an aluminum housing. Aluminum was used as the housing material because aluminum is nontoxic and can be easily sterilized. In addition, aluminum exhibits a low acoustic loss and a low characteristic acoustic impedance (about 17.3 MRayls), relative to most metals. Thus, aluminum represents a suitable material for use as an acoustic matching layer. A thin tube having a diameter of 3 mm was used for handle 24. Coaxial power cables were disposed within the tube. The front surface of the aluminum housing was glued to the PZT element under pressure (in a specially designed silicone rubber mold) using degassed non-conductive epoxy. The electrical connection to the lead wire of the coaxial cable was achieved using brass snipes glued to the back of the PZT element with silver epoxy. The ground connection to the front surface of the PZT element was achieved through the aluminum housing. The electrical impedance matching circuitry of the device was implemented using a transformer (3:5 core ratio) and a 270 pF capacitor.

The resonant frequency and quality (Q) factor of the device were measured using an impedance analyzer. The ultrasound field was observed using Schlieren imaging and hydrophone field mapping. The acoustic power was measured with reflective radiation force balance. The first empirical thin-profile TOFU device had a resonant frequency of 6.26 MHZ, a bandwidth of 0.17 MHz, and a Q factor of 37. Schlieren images showed a sharp focus (dimensions in order of mm) at a distance of 3 cm from the transducer. Sharp focusing was observed with Schlieren imaging. The fill-width half-maximum (FWHM) dimensions of the focal region were 0.6 mm and 2.2 mm in the lateral and the axial direction, respectively. The −3 dB cross-sectional area of the focus was 0.003 cm. The transducer efficiency was 42%, indicating that the aluminum front surface at the thickness of ¾ wavelength provided good acoustic matching. Acoustic output powers of up to 28.5 W were measured, which correspond to intensities of up to 9,500 W/cm$^2$ at the focus (in water). HIFU application for 10 seconds at an intensity of 6,170 W/cm$^2$ (in situ) produced lesions in the gel phantom. Lesions were also produced in the rabbit kidney in vivo (10 seconds at an intensity of 5,485 W/cm$^2$).

Figure 3B:
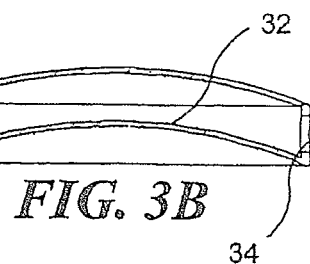
FIG. 3B is a cross-sectional view of the aluminum housing of FIG. 3A.

FIGS. 3A and 3B illustrate details of therapy head 22 in the first empirical device. FIG. 3A is an exploded schematic view of an aluminum housing 30, a concave PZT therapy transducer 36, and a cover plate 38. Aluminum housing 30 includes a concave surface 32 (configured to support the corresponding concave PZT therapy transducer), and an opening 34 configured to enable the coaxial cable running through the elongate handle to be electrically coupled to the PZT transducer and the aluminum housing, generally as described above.

FIG. 3B is a cross-sectional view of aluminum housing 30, enabling concave surface 32 to be better visualized. Cover plate 38 was implemented using a transparent plastic plate to enable the PZT element to be observed. It should be recognized that an opaque plate can also be used, and that other materials, such as aluminum, can be used for the cover plate.

Based on the success of the first empirical device, which conformed to acoustic device 20 of FIG. 1B, additional HIFU applicators were produced, having operating frequencies of 3 MHz and 3.5 MHz. Each additional device included an air-backed concave PZT element (e.g., one obtained from American Piezo Ceramics, Inc., Mackeyville, Pa.), an aluminum housing and a semi-transparent cover plate. While the first empirical device employed a PZT-4 element, the latter two devices used PZT-8 elements. Each PZT element had a diameter of about 3.5 cm. The initial device had a focal length/radius of curvature of 3.5 cm, while the latter devices had a focal length/radius of curvature of 5 cm. The thickness of the aluminum housing in front of the transducer was ¾ of the ultrasound wavelength (in aluminum) for the initial device, and ¼ of the ultrasound wavelength (in aluminum) for the latter two devices. In each device, that portion of the aluminum housing served as a matching layer for the transducer.

Each PZT element was bonded to the aluminum housing using a non-conductive epoxy (for example, one produced by Duralco 4461, Cotronics Corp, Brooklyn, N.Y.), although other types of adhesive may be used. The resin was first heated, to reduce the viscosity, and then degassed to remove trapped air bubbles. Once bonded, the element and housing were allowed to cure under pressure using a form fitting silicone rubber mold. A relatively short aluminum tubular fitting was bonded to opening 34 in the aluminum housing using silver conductive epoxy (for example, a type E-Solder 3022, available from Von Roll Isola, New Haven, Conn.). Electrical connections were made via coaxial cable (RG-58, Belden Electronic Division, Richmond, Ind.), as schematically illustrated in FIGS. 3A-3E. Other comparable epoxy and cables can be used, instead.

Coaxial cable 50 includes an inner conductor 42, insulation 48, and an outer grounding conductor 44. The inner conductor, with insulation, reached the back of the PZT element though the fitting where it was soldered in place. The outer ground conductor was positioned around tubular fitting 40, and a metal sleeve 46 (i.e., the crimp splice cap) was crimped around the conductor, trapping the conductor between the sleeve and the tubular fitting. The second electrical connection grounded the aluminum housing and protected the soldered connection by absorbing forces applied to the cable. The ground connection was shrink wrapped to prevent fluid leakage into the housing. The semitransparent cap was then bonded to the housing, sealing each device. Note that FIG. 4A is a cross-sectional view of the electrical connection components. FIG. 4B shows the inner conductor being inserted through crimp splice cap. FIG. 4C shows the inner insulation and the inner conductor being inserted into the aluminum tubular fitting with the outer grounding conductor wrapped around the tubular fitting. FIG. 4D shows the crimp splice cap being slid along the coaxial cable and around the outer grounding conductor, and FIG. 4E shows the crimp splice cap being crimped to the tubular fitting and the outer grounding conductor. These various details are intended to be exemplary and not limiting on the scope of this technology.

For each device, an electrical impedance matching network was made to maximize the transmitted electrical power to the transducer by adjusting the impedance of the device. The resonant frequency and corresponding real and imaginary impedances were determined with an impedance analyzer (in this case, a model 4914A, available from Hewlett Packard, Palo Alto, Calif.) with the device operating in water. A matching circuit shown in FIG. 4F was built such that the real and imaginary impedances were approximately 50Ω and 0Ω, respectively. The completed HIFU applicators and their respective matching networks were analyzed to verify electrical matching.

For each of the three empirical devices discussed above, the HIFU beam was visualized using Schlieren imaging and hydrophone field mapping. Schlieren measurements were performed in a tank of degassed water with 10 W of electrical power supplied to the transducer. A digital camera (a model C700UZ from Olympus, Tokyo, Japan) was used to capture the images. For the field mapping, a needle hydrophone (a model TNU001A from NIR Systems, Inc., Seattle, Wash.) with a spatial resolution of 0.6 mm was used to map the axial and lateral dimensions of the HIFU beam. The HIFU transducer was placed in a tank of degassed water where the hydrophone was moved with stepping motors. The −3 dB focal area was determined using a custom-written program (NATLAB, Mathworks, Natick, Mass.).

The acoustic power output for each of the three devices was measured using a radiation force balance (a model UPM-DT-10 from Ohmic Instruments Co., Easton, Md.). The incident power applied to the transducer was varied, in 5 W increments, from 5 W to 100 W, or until the acoustic power output became unstable. The measured acoustic power was compared to the incident electrical power to determine the efficiency of each device. The focal intensity in water was calculated using the acoustic power and the −3 dB cross-sectional area of the focus. The average acoustic efficiency (the ratio of acoustic power output to incident electric power), was 42±2% for the first device, 33±1% for the second device, and 36±3% for the third device. Each of the thin-profile applicators was able to generate a "tadpole-shaped" lesion in the tissue-mimicking gel. The HIFU-treated lesions were, on average, about 8 mm wide and 5 mm deep.

While the three empirical thin-profile HIFU devices discussed exhibited good performance, the external water pillow cooling configuration undesirably increased the thickness of the device. In order to achieve a thin-profile HIFU applicator that did not require an external water pillow for cooling, additional designs incorporating fluid channels within the aluminum housing were investigated.

FIG. 5A schematically illustrates a therapy head housing 60 incorporating a fluid channel 64 disposed about the periphery of the housing. A concave transducer (not separately shown) is introduced into an inner volume 62. It should be understood that inner volume 62 includes a surface configured to engagingly support the concave transducer, generally as discussed above with respect to FIGS. 3A and 3B. A fluid inlet 66a and a fluid outlet 66b enable a cooling fluid (such as water) to be circulated through fluid channel 64, to remove heat generated by the transducer. An opening 68 enables the transducer to be electrically coupled to a power source, generally as described above with respect to FIGS. 4A-4E. FIG. 5B is a cross-sectional view of therapy head housing 60. Note that the housing has a surface 70 that functions as an acoustical lens.

The engineering program ANSYS™ was used to model the housing incorporating the fluid channel about the periphery of the housing. Because modeling an acoustic lens is difficult in ANSYS, a simplified version of the housing, without the curvature of the lens, was modeled instead. FIG. 6 schematically illustrates the simplified model with the dimension variables identified. The variables include the following:

C_H: Channel height
C_W: Channel width
CW_T: Channel wall thickness
T_H: Lens height
T_W: Lens diameter
X1: Outer channel width=CW_T+C_W+CW_T
Y1: Outer channel height=T_H+C_H+CW_T Parameters that were constants or not varied in the analysis include the following:

Specific heat of aluminum—900 J/kg° K
Specific heat of water—4181.9 J/kg° K
Thermal conductivity of aluminum—151 W/m° K
Thermal conductivity of water—0.609 W/m° K
Density of aluminum—2820 kg/m$^3$
Density of water—998.23 kg/m$^3$
Initial temperature of system—295° K The default values of the independent variables employed are as follows:

Thermal heat generation (power from transducer lost to heat)—75 J/S
Heat transfer to water coefficient—845 W/m$^{2°}$ K
Heat transfer to air coefficient—12 W/m$^{2°}$ K
CW_T—0.001 m
C_W0.002 m
C_H—0.00375 m
T_W—0.0175 m
T_H—0.00092 m The dependent variables to be measured are as follows:
maximum temperature of lens (° K)
time until hottest point (350° K) was reached 350° K (s)
time until a steady state was reached (s)

A series of simulations were performed for each independent variable. Values used for the independent variables were systematically increased and decreased, and the values for the dependent variables were measured, and then plotted. The results are graphically illustrated in FIGS. 7A-7H.

The accuracy of the dependent variables cannot be determined because the simulation was based on a simplified model, as opposed to an empirical device. However, the simplified model is still useful for identifying how the dependent variables change in relationship to changes in the independent variables. For example, the data graphically illustrated in FIGS. 7A-7H indicate that for most of the independent variables, changes in the independent variable did not generate a significant change in the maximum temperature (any temperature change was generally limited to a few degrees). The data from the analysis of the simple model do suggest that the variables having the largest effect on temperature are the lens diameter and the lens thickness. Significantly, when increased, these variable increase the mass of the housing, providing a larger mass of aluminum to absorb more heat.

The above results led to an exemplary modified housing/lens combination, which is schematically illustrated in FIGS. 8A-8B. FIG. 8A is a cross-sectional isometric view of a housing 80, which incorporates an inner volume 82 having a surface 84 configured to support a flat transducer (not separately shown), a peripheral fluid channel 90, and a curved surface 86 configured to function as an acoustic lens. In one exemplary embodiment, the housing is fabricated of aluminum, and a thickness at about a center 88 of the acoustic lens is equivalent to about a full wavelength (in aluminum) of the acoustic beam produced by the ultrasound transducer when energized. The thickness of the acoustic lens used in this embodiment was derived based on a series of empirical studies using different thicknesses. The result was somewhat surprising, since other studies involving determining an optimal thickness for an aluminum matching layer for a concave transducer yielded a different optimal thickness (i.e., ¾ of a wavelength). Furthermore, the thickness of about one wavelength appears to be independent of factors such as transducer wavelength (i.e., different wavelength transducers can be used), the focal length of the acoustic lens, or the diameter of the acoustic lens. In one exemplary embodiment, the surface in the aluminum housing acting as an acoustic lens is elliptical, rather than spherical.

FIG. 8B is a plan view of an exemplary housing 80, illustrating a fluid inlet 92a, a fluid outlet 92b, and an opening 94 (to enable the transducer to be electrically coupled to a power source, generally as described above). Note that housing 80 includes a block portion 96 encapsulating fluid inlet 92a, fluid outlet 92b, and opening 94. Block portion 96 both provides additional support for coupling fluid lines and the handle into their respective openings, and provides additional mass (which beneficially increases an amount of thermal energy the housing can absorb from the transducer).

FIG. 9 is a side view of housing 80 showing exemplary dimensions in millimeters (i.e., these dimensions are not limiting). Clearly, this design enables a low-profile HIFU therapy head to be achieved. The relationship of a transducer 98 to inner volume 82, and surfaces 84 and 86 can be readily visualized in this Figure. The piezoelectric crystal is bonded to the aluminum housing using an epoxy glue, but other types of glue might instead be used. It should be noted that care should be taken to eliminate any bubbles in the epoxy adhesive layer, because such bubbles would interfere with the transmission of the acoustic beam through the epoxy layer. Preferable dimensions will maintain the height of the transducer and housing to about 1 cm, while the diameter varies from about 2 cm to about 12 cm, and the focal length varies from about 2 cm to about 12 cm. Preferably, the f-number of the HIFU transducer (i.e., the focal length over the diameter) ranges from about 1 to about 1.5. Such dimensions are intended to be exemplary.

FIG. 10A is an exploded isometric view of an exemplary thin-profile HIFU therapy head incorporating housing 80. Barb fittings 100 are provided in fluid inlet 92a and fluid outlet 92b, to enable distal ends of flexible tubing 106 to be attached to the thin-profile HIFU therapy head. The proximal ends of the flexible tubing will be attached to a circulating water pump (not separately shown) to provide a cooling flow of water through peripheral channel 90. The components discussed in detail above, in connection with FIGS. 4A-4E (the same reference numbers have been used in FIG. 10A), enable the required electrical energy to be provided to the transducer, generally as explained above. If desired, an elongate hollow tubular handle (not specifically shown in FIG. 10A, although such an element is shown in FIG. 1B) can be placed over coaxial cable 50 to provide a more rigid handle. If a flexible handle is desired, the coaxial cable itself can serve as the handle. If desired, the flexible tubing and the coaxial cable can be covered by a flexible or rigid, or semi-rigid sheath 108 (FIG. 10B), such that the sheath serves as the handle.

A cover 104 is secured to housing 80 to seal inner volume 82. Once sealed, inner volume 82 and cover 104 provide an air-backed chamber for transducer 98. FIG. 10B is an isometric view of the assembled thin-profile HIFU therapy head. Cover 104 can be fabricated using the same material as housing 80 (i.e., aluminum or some other suitable metal), or a different material (such as the transparent plastic employed in the empirical devices discussed above).

Housing 80 (including the integrated peripheral cooling channel and an acoustic lens) enables a relatively cheaper HIFU applicator to be achieved, because flat transducers are generally significantly less expensive than curved or concave transducers. Because a flat transducer is used, it is important that the housing include the acoustic lens portion, to enable focusing of the HIFU beam. In the thin-profile HIFU applicators discussed above, the concave piezoelectric crystals provides natural focusing of the HIFU beam, and an acoustic lens is not required. Because the internal fluid channel is provided for conveying cooling liquid, the external water pillows or expandable balloons are not required to provide cooling. While such external water pillows and expandable balloons provide acoustic coupling and cooling, these components require additional setup time, and can be cumbersome to work with in an intra-operative environment, because they increase the size of the overall HIFU therapy apparatus. In contrast, the exemplary thin-profile HIFU therapy apparatus of FIGS. 9A and 9B can be acoustically coupled to target tissue using conventional coupling gels, or extremely thin pillows, which do not need to convey a fluid for cooling the transducer. Additional simulations based on the new housing (i.e., housing 80) were performed, and the results indicated that the new design provided an additional 30° of cooling. Water can be used as a cooling fluid, although other fluids, such as glycols (or any other fluid with good cooling properties), can also be employed. Note that because the fluid is not disposed in the path of the ultrasound beam, the cooling fluid need not be de-gassed, which is a requirement when using a latex balloon (or water pillow), as the cooling fluid in such devices is disposed between the transducer and the target.

As noted above, analytical modeling and empirical tests have indicated that when a flat transducer and an aluminum acoustic lens are employed, a thickness at about a center of the acoustic lens can be about a full wavelength (in aluminum) of the acoustic beam produced by the ultrasound transducer. FIG. 11A graphically illustrates such a result for the first transducer and lens combination, while FIG. 11B schematically illustrates this result for a second transducer and lens combination, indicating that the optimal thickness at a center of the acoustic lens of a full wavelength is valid for different transducer and lens combinations. The optimal thickness does not appear to be dependent on the diameter of the lens or PZT element, and also appears to be independent of the frequency and focal length of the ultrasound (other than being related to the wavelength chosen).

As noted above, when attaching either a concave or flat transducer to a housing, the quality of the adhesive layer (high quality implying an adhesive layer that is relatively bubble-free) is important in obtaining a durable and high performance HIFU therapy applicator. The following techniques have been developed and empirically tested to enhance a quality of the adhesive layer coupling the transducer to the housing/acoustic lens.

Before attempting to attach the transducer to the housing or lens, it is important that all surfaces be clean. The following items can be used to clean the components: an ultrasonic cleaner, distilled water, tweezers, beakers, a fiberglass brush, sandpaper, and compressed air. A useful cleaning procedure is as follows.

Clean the tools and containers in the ultrasonic cleaner using distilled water. Remove the oxide layer on the negative (i.e., the grounding) surface of the piezoceramic crystal by very slightly brushing with the fiberglass brush. The positive side of the piezoceramic crystal is generally marked with a black dot by the manufacturer, enabling the negative and positive sides of the transducer to be readily identified. The negative side will ultimately be adhesively coupled to the aluminum lens (or aluminum housing). Use the sandpaper to clean and condition the side of the aluminum lens/housing that will be bonded with the transducer (280 grit sandpaper can be beneficially employed for this purpose). Besides removing any oxidation, the function of the sandpaper is to introduce very minor imperfections onto the aluminum surface, as such imperfections provide something for the adhesive to bite or grab onto. If the transducer is flat, the flat side of the aluminum lens will be conditioned. As noted above, the resulting conditioned surface will enhance the bond between the transducer and the aluminum lens/housing. Fill a beaker with a detergent solution, and place the transducer into the detergent solution. Place the beaker with the detergent and the transducer into the ultrasonic cleaner (about five seconds should be sufficient, over sonification should be avoided). Rinse the cleaned transducer using distilled water. The aluminum lens/housing is then placed in the beaker with the detergent solution, cleaned in the ultrasonic cleaner (for about 20 seconds or more; there is little risk of over sonification), and then rinsed using distilled water. Dry both the crystal and the lens using the compressed air. The transducer and aluminum lens/housing are now ready for gluing.

An exemplary gluing procedure is as follows. Fill a beaker with water and place the beaker and water on a hot plate. Measure an appropriate amount of resin and hardener (an exemplary resin is Duralco 4461 resin and the corresponding hardener), using a ratio of 100:17 by mass. The resin and hardener can be transferred using a wooden stick and weighed in an aluminum weighing dish sufficiently large to accommodate the resin and hardener without mixing the two. Place the aluminum weighing dish in the beaker full of hot water (the water can be near boiling). Heating the resin and hardener will make them less viscous. Gently stir the resin into the hardener to mix them together. Preferably, the heating procedure should be as short as possible. Significantly, the epoxy should not be heated to its own boiling point, as this would generate bubbles within the epoxy. Spread the mixed resin and hardener over the bottom surface of the aluminum dish in a thin layer over heat, to cause any bubbles to collapse. Bubbles can also be eliminated by tilting the aluminum dish to trap the mixed epoxy in one corner of the dish, and then rotating the aluminum dish to cause the epoxy to flow along the rim of the aluminum dish. Both techniques are beneficially used to reduce bubbles. Check the epoxy using a microscope to determine if any bubbles remain, and if so, continue the procedure explained above to remove any remaining bubbles. Expose the epoxy in the aluminum dish to a moderate vacuum for about five minutes, such that any bubbles entrapped in the epoxy are drawn out by the reduced pressure in the vicinity of the epoxy. Check using a microscope once again, and repeat the bubble removal procedure as necessary. Reheat the dish, and trap the epoxy in one corner of the dish by tilting the dish. Bend a portion of the aluminum dish to form a spout. Pour a few drops of the epoxy into the center of the aluminum lens/housing, concentrated in one spot. Slowly place the negative side of the transducer against the aluminum lens/housing. Place the transducer and aluminum lens/housing between a form fitting elastomeric mold. Apply pressure and let the epoxy dry for an extended period of time (preferably at least 24 hours, although the specific time may vary based on the specific resin/hardener employed).

After the transducer is coupled with the aluminum housing/lens, the center core lead of a coaxial cable is soldered to the center of the crystal. Conductive silver epoxy (E-Solder 3022, Von Roll Isola, Schenectady, N.Y., USA) is used to affix the grounding wire to the aluminum housing/lens. It should be noted that while exciting the crystal, the heat may cause the conductive epoxy to flake off. Thus, it is recommended to provide a mechanical connection (such as clamping or crimping) to affix the wire to the crystal, in addition to the conductive epoxy. Waterproof epoxy can be placed over the conductive epoxy (which is not waterproof) to seal the conductive epoxy. The waterproof epoxy is also used to attach the cover over the inner volume housing the transducer (to achieve the air-backed transducer configuration discussed above).

The above described procedure for gluing the transducer to the housing worked well with transducers ranging from 3-5 cm in diameter. The following technique was developed for a larger 12.5 cm flat transducer. Because of the much larger surface area of this transducer, there exists a greater chance for trapping bubbles in the adhesive layer coupling the transducer to the lens. Because ultrasound cannot propagate in air, bubbles in the epoxy layer between the crystal and the lens will cause serious transmission problems, and may even destroy the HIFU transducer. In the gluing process, there are three primary ways in which bubbles become trapped in the adhesive layer: (1) while mixing the resin and the hardener; (2) while pouring the mixed resin and hardener onto the lens; and, (3) while joining the transducer (i.e., the crystal) and lens together. The larger the crystal, the more important it is to achieve a substantially bubble-free adhesive layer. To this end, a series of 6-inch diameter acrylic circles were glued together using different techniques. The resulting adhesive layers could then be evaluated under magnification to evaluate the amount of bubbles in the adhesive layers obtained using the different techniques. The following modifications to the above described technique were identified as yielding the most bubble-free adhesive layer.

The use of a finer grit sandpaper to condition the aluminum lens (or aluminum housing) yielded a higher quality adhesive layer. In empirical studies, 600 grit sandpaper worked better than 280 grit sandpaper. The coarser sandpaper results in a greater mean surface roughness on the aluminum lens. Some roughness or imperfections are required to enhance bonding, but too much roughness/imperfections provides scratches in which air bubbles can become trapped.

Instead of pouring epoxy only on the center of the aluminum lens, equal amounts of epoxy should be poured in the center of the aluminum lens and the transducer.

The aluminum should be preheated to prevent the epoxy from solidifying quickly. Once again, it is important that the temperature of the epoxy not approach its own boiling point, to prevent the introduction of bubbles into the epoxy.

Before joining the transducer to the lens, invert either the transducer or the aluminum lens until the epoxy begins to drip. Position the drip immediately over the epoxy on the other of the transducer and aluminum lens, and mate the aluminum lens and the transducer together (so that the drip that is still connected and the pool of epoxy on the other surface join together at that time).

It was also determined that the above described cleaning method was not suitable for a larger diameter aluminum lens and flat transducer. A modified cleaning procedure is described as follows. Fine sandpaper (preferably 600 grit) is used to roughen the negative surface of the crystal and the surface of the aluminum lens to which the crystal will be adhered. Flush each roughened surface under running water for a minute or more. Soak the crystal and the aluminum in the detergent solution for more than a minute after rinsing. Flush the roughened surfaces in running water again (to remove the detergent). Dry the crystal and the aluminum using compressed air.

FIGS. 12A and 12B schematically illustrate an embodiment of a thin-profile HIFU therapy applicator that does not include an elongate handle, such that a clinician simply grasps the therapy head, and directly manipulates the therapy head to selectively position the HIFU focal point. Thus, in at least one embodiment, no handle is attached to the therapy head. Instead, a clinician simply grasps the therapy head itself, and moves the therapy head to the treatment site. A strap can be added to secure the therapy head to the clinician's hand. FIG. 12A schematically illustrates a clinician holding a thin-profile HIFU therapy head 120 (generally consistent with those described above) in a hand 126, to position an acoustic beam 128 emitted by therapy head 120, such that a focal point 130 of the acoustic beam overlaps a treatment site 122 in a patient 124. While the thin-profile therapy heads disclosed herein are particularly well suited for internal treatment sites, it should be recognized that the thin-profile devices disclosed herein can be used externally as well. Manipulating an elongate handle to selectively position a therapy head is a more complex task than simply manipulating the therapy head directly. As long as the therapy head is sufficiently cooled, the clinician should not experience discomfort while holding the therapy head. Furthermore, the clinician can wear heat resistant gloves (not specifically shown), to further reduce any discomfort that might be encountered because of heat generated by the therapeutic transducer.

In FIG. 12B, the thin-profile device of FIG. 10B (generally indicated by housing 80) has been modified by adding a strap 132, the strap being configured to secure the thin-profile device to a clinician's hand (i.e., hand 126). It should be recognized that strap 132 can be implemented using a wide variety of materials, such as textiles, hook and loop fasteners, and elastomeric materials. If desired, strap 132 can include a buckle 134 to enable the strap to be tightened. In other embodiments, strap 132 is sufficiently flexible to enable an interference fit to be achieved with a wide variety of different hand sizes and shapes, such that the buckle or other adjustment device is not required. Note that as illustrated in FIG. 12B, an arm 136 of the clinician, flexible tubing 106, and coaxial cable 50 are all generally aligned along an axis 138. While such a configuration is not required, aligning the flexible tubing and the coaxial cable with the clinician's arm will ensure that the flexible tubing and the coaxial cable are out of the way. If desired, additional straps (not specifically shown) could be used to secure the coaxial cable and flexible tubing to the user's forearm, to ensure that the flexible tubing and the coaxial cable do not interfere with the clinician's ability to manipulate the therapy head.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. Apparatus for ultrasound therapy, comprising:
   (a) a therapy head including:
      (i) an ultrasound transducer configured to generate therapeutic ultrasound when energized; and
      (ii) a housing including an inner volume in which the ultrasound transducer is disposed, the housing being configured to support and encompass the ultrasound transducer and further including a fluid channel disposed to circumscribe a periphery of at least a portion of the housing, the fluid channel having an inner wall that separates the fluid channel from the inner volume and being configured to enable a cooling fluid to be circulated within the fluid channel and circumscribe the periphery of at least the portion of the housing so as to provide cooling of the ultrasound transducer that is disposed in the inner volume while the cooling fluid is circulated within the fluid channel.

2. The apparatus of claim 1, further comprising:
   (a) an electrical conductor extending beyond the therapy head, the electrical conductor being configured to enable the ultrasound transducer to be selectively energized;
   (b) a fluid intake conduit in fluid communication with the fluid channel, the fluid intake conduit extending beyond the therapy head and being configured to introduce a cooling fluid into the fluid channel; and
   (c) a fluid outtake conduit in fluid communication with the fluid channel, the fluid outtake conduit extending beyond therapy head and being configured to remove cooling fluid from the fluid channel.

3. The apparatus of claim 1, further comprising a generally elongate handle coupled to the therapy head, the generally elongate handle enabling a clinician to manually manipulate and selectively position the therapy head proximate a treatment site.

4. The apparatus of claim 1, further comprising a strap coupled to the therapy head, the strap enabling the therapy head to be secured to a clinician's hand.

5. The apparatus of claim 1, wherein the housing comprises aluminum.

6. The apparatus of claim 1, wherein the housing is generally spoon-shaped, a surface of the housing being generally concave.

7. The apparatus of claim 1, wherein the therapy head has a thickness that is substantially less than its diameter, such that the therapy head exhibits a low-profile configuration.

8. The apparatus of claim 1, wherein a portion of the housing defining the inner volume comprises an acoustic lens, the acoustic lens being configured to focus an acoustic beam emitted from the ultrasound transducer toward a treatment site, when the ultrasound transducer is energized.

9. The apparatus of claim 1, wherein the ultrasound transducer comprises a concave transducer element, and wherein the inner volume is configured with an appropriate surface with which to receive and contact the concave transducer element.

10. The apparatus of claim 1, wherein the ultrasound transducer comprises a flat transducer element, and wherein the inner volume is configured to receive the flat transducer element.

11. The apparatus of claim 1, wherein the inner wall comprises a plurality of grooves configured to increase a surface area of the inner wall, to enhance cooling of the ultrasound transducer that is disposed within the inner volume.

12. The apparatus of claim 1, wherein the ultrasound transducer comprises a concave transducer element, and a thickness at about a center of an acoustic lens portion of the housing separating the ultrasound transducer from an ambient volume ranges from about ¼ to about ¾ of a wavelength of the ultrasound produced by the ultrasound transducer when energized.

13. The apparatus of claim 1, wherein the ultrasound transducer comprises a concave transducer element, and a thickness at about a center of an acoustic lens portion of the housing separating the ultrasound transducer from an ambient volume is about ¾ of a wavelength of the ultrasound produced by the ultrasound transducer when energized.

14. The apparatus of claim 1, wherein the ultrasound transducer comprises a flat transducer element, and a thickness at about a center of an acoustic lens portion of the housing separating the ultrasound transducer from an ambient volume is equal to about one wavelength of the ultrasound produced by the ultrasound transducer when energized.

15. The apparatus of claim 1, wherein the inner volume is larger than the ultrasound transducer, enabling an air-backed ultrasound transducer configuration to be achieved.

16. The apparatus of claim 1, wherein the housing is about 4 centimeters in diameter and about 1 centimeter in thickness, and wherein the ultrasound transducer has a focal length of about 3.5 centimeters.

17. Apparatus for administering an ultrasound therapy, comprising:
   (a) a therapy head including:
      (i) an ultrasound transducer configured to generate therapeutic ultrasound when energized; and
      (ii) a housing in which the ultrasound transducer is disposed, the housing including an inner volume configured to support and encompass the ultrasound transducer and further including a fluid channel disposed to circumscribe a periphery of at least a portion of the housing, the fluid channel having an inner wall that separates the fluid channel from the inner volume and being configured to enable a cooling fluid to be circulated within the fluid channel and circumscribe the periphery of at least the portion of the housing so as to cool the ultrasound transducer that is disposed in the inner volume while the cooling fluid is circulated within the fluid channel, a portion of the housing proximate the inner volume comprising a curved surface functioning as an acoustic lens configured to focus an acoustic beam emitted from the ultrasound transducer when the ultrasound transducer is energized; and
   (b) an electrical conductor extending beyond the therapy head, the electrical conductor being configured to enable the ultrasound transducer to be selectively energized.

18. The apparatus of claim 17, further comprising a generally elongate handle coupled to the therapy head, the generally elongate handle enabling a clinician to manipulate and selectively position the therapy head proximate a treatment site.

19. The apparatus of claim 17, further comprising a strap coupled to the therapy head, the strap enabling the therapy head to be secured to a clinician's hand.

20. The apparatus of claim 17, wherein the housing comprises aluminum.

21. The apparatus of claim 17, wherein the fluid channel is further configured to couple to a source of the cooling fluid.

22. The apparatus of claim 21, wherein the inner wall comprises a plurality of grooves configured to increase a surface area of the inner wall, to enhance cooling of the ultrasound transducer that is disposed in the inner volume.

23. The apparatus of claim 17, wherein the ultrasound transducer comprises a concave transducer element, and a thickness at about a center of the acoustic lens is an odd multiple of about ¼ of a wavelength of the acoustic beam produced by the ultrasound transducer when energized.

24. The apparatus of claim 17, wherein the ultrasound transducer comprises a flat transducer element, and a thickness at about a center of an acoustic lens portion of the housing separating the ultrasound transducer from an ambient volume is equal to a multiple of about one full wavelength of the ultrasound produced by the ultrasound transducer when energized.

25. A method for providing ultrasound therapy, comprising the steps of:
   (a) positioning a therapy probe proximate a treatment site;
   (b) energizing an ultrasound transducer disposed in the therapy probe to deliver therapeutic ultrasound to the treatment site; and
   (c) cooling the ultrasound transducer by circumscribing a cooling fluid around a periphery of at least a portion of a housing of the therapy probe in which the ultrasound transducer is disposed such that the ultrasound transducer is cooled while the cooling fluid is circumscribed around the periphery and without substantially contacting the ultrasound transducer.

26. The method of claim 25, wherein the housing of the therapy probe comprises an inner volume configured to support and encompass the ultrasound transducer, the housing including a fluid channel that circumscribes at least a portion of the periphery of the inner volume, and wherein the step of cooling the ultrasound transducer comprises the step of circulating the cooling fluid in the fluid channel within the housing, the fluid channel being disposed between the inner volume and an outer surface of the housing.

27. The method of claim 25, further comprising the step of focusing the therapeutic ultrasound with an acoustic lens that is part of the housing.

28. The method of claim 27, wherein the step of focusing the therapeutic ultrasound comprises the step of using an acoustic lens for focusing a concave transducer element, the acoustic lens having a minimum thickness ranging from about ¼ to about ¾ of a wavelength of the ultrasound delivered by the concave transducer element.

29. The method of claim 27, wherein the step of focusing the therapeutic ultrasound comprises the step of using an acoustic lens for focusing a flat transducer element, the acoustic lens having a minimum thickness equal to about one full wavelength of the ultrasound delivered by the flat transducer element.

* * * * *

UNITED STATES PATENT AND TRADEMARK OFFICE
CERTIFICATE OF CORRECTION

PATENT NO. : 8,414,494 B2
APPLICATION NO. : 12/065768
DATED : April 9, 2013
INVENTOR(S) : Vaezy et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1275 days.

Signed and Sealed this
Sixteenth Day of December, 2014

Michelle K. Lee
*Deputy Director of the United States Patent and Trademark Office*